(12) United States Patent  
Nguyen et al.

(10) Patent No.: US 10,022,475 B2  
(45) Date of Patent: Jul. 17, 2018

(54) BODY AUGMENTATION DEVICE

(71) Applicants: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(72) Inventors: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(73) Assignee: Bao Tran, Saratoga, CA (US)

( * ) Notice: Subject to any disclaimer, the term of this patent is extended or adjusted under 35 U.S.C. 154(b) by 0 days.

(21) Appl. No.: 15/409,544

(22) Filed: Jan. 19, 2017

(65) Prior Publication Data

US 2017/0232148 A1   Aug. 17, 2017

Related U.S. Application Data

(63) Continuation-in-part of application No. 14/255,967, filed on May 1, 2014, now Pat. No. 9,220,807, and a
(Continued)

(51) Int. Cl.
| | | |
|---|---|---|
| *A61F 2/12* | (2006.01) | |
| *A61L 27/52* | (2006.01) | |
| *A61F 2/00* | (2006.01) | |
| *A61M 5/19* | (2006.01) | |
| *A61M 5/315* | (2006.01) | |
| *A61L 27/20* | (2006.01) | |
| *C08J 3/24* | (2006.01) | |
| *A61L 27/54* | (2006.01) | |
| *A61K 31/496* | (2006.01) | |
| *A61L 27/16* | (2006.01) | |
| *C08J 3/075* | (2006.01) | |
| *C08J 3/28* | (2006.01) | |

(52) U.S. Cl.
CPC ............ *A61L 27/52* (2013.01); *A61F 2/0059* (2013.01); *A61F 2/12* (2013.01); *A61K 31/496* (2013.01); *A61L 27/16* (2013.01); *A61L 27/20* (2013.01); *A61L 27/54* (2013.01); *A61M 5/19* (2013.01); *A61M 5/31596* (2013.01); *C08J 3/075* (2013.01); *C08J 3/246* (2013.01); *C08J 3/28* (2013.01); *A61L 2300/406* (2013.01); *A61L 2300/41* (2013.01); *A61L 2400/06* (2013.01); *A61L 2430/04* (2013.01); *C08J 2329/04* (2013.01); *C08J 2405/08* (2013.01)

(58) Field of Classification Search
CPC ................................ A61F 2/12; A61K 38/363
USPC ................... 623/11.11, 7–8, 23.65–23.76
See application file for complete search history.

(56) References Cited

U.S. PATENT DOCUMENTS 5,012,503 A * 4/1991 Nambu ................. A61L 2/0035
378/64
6,268,405 B1 * 7/2001 Yao ......................... A61L 27/16
264/28
(Continued)

*Primary Examiner* — Suzette J Gherbi
(74) *Attorney, Agent, or Firm* — Tran & Associates

(57) ABSTRACT

Systems and methods are disclosed for body augmentation by mixing hyaluronic acid (HA) with polyvinyl alcohol (PVA) to form an HA-PVA hydrogel; and exposing the HA-PVA hydrogel to one or more freeze-thaw cycles or to an amount of radiation effective to crosslink the HA to the PVA to crosslink the HA to the PVA.

20 Claims, 15 Drawing Sheets

Related U.S. Application Data continuation of application No. 14/881,028, filed on Oct. 12, 2015, now Pat. No. 9,561,095.

(56) References Cited

U.S. PATENT DOCUMENTS

| | | | | |
|---|---|---|---|---|
| 6,881,226 B2* | 4/2005 | Corbitt, Jr. | A61F 2/12 | 424/400 |
| 7,998,201 B2* | 8/2011 | Lesh | A61F 2/0059 | 623/11.11 |
| 7,998,202 B2* | 8/2011 | Lesh | A61F 2/0059 | 623/11.11 |
| 8,383,161 B2* | 2/2013 | Campbell | A61L 27/50 | 424/502 |
| 9,039,763 B2* | 5/2015 | Corbitt, Jr. | A61F 2/0059 | 623/7 |
| 2004/0006296 A1* | 1/2004 | Fischell | A61B 17/06166 | 602/48 |
| 2004/0047892 A1* | 3/2004 | Desrosiers | A61L 27/20 | 424/423 |
| 2005/0187639 A1* | 8/2005 | Hunter | A61K 38/17 | 623/23.72 |
| 2008/0159608 A1* | 7/2008 | Suetens | G06T 19/20 | 382/128 |
| 2009/0053276 A1* | 2/2009 | Richard | A61K 9/0019 | 424/422 |
| 2009/0181104 A1* | 7/2009 | Rigotti | A61F 2/12 | 424/574 |
| 2011/0142936 A1* | 6/2011 | Campbell | A61L 27/50 | 424/484 |
| 2011/0150846 A1* | 6/2011 | Van Epps | A61L 27/3839 | 424/93.7 |
| 2012/0039980 A1* | 2/2012 | Daniloff | A61K 9/1075 | 424/422 |
| 2012/0128746 A1* | 5/2012 | Maitra | A61K 8/891 | 424/401 |
| 2012/0165935 A1* | 6/2012 | Van Epps | A61L 27/3839 | 623/8 |
| 2013/0012683 A1* | 1/2013 | Daniloff | A61K 9/0024 | 528/372 |
| 2013/0273115 A1* | 10/2013 | Nguyen | A61K 9/0014 | 424/400 |
| 2014/0058009 A1* | 2/2014 | Choi | A61L 27/16 | 523/113 |
| 2014/0329756 A1* | 11/2014 | Nguyen | A61K 9/0024 | 514/17.2 |
| 2015/0190517 A1* | 7/2015 | Nguyen | A61K 47/36 | 514/180 |

* cited by examiner

| storing a non-toxic biocompatible cross-linker in a first volume (702) |
|---|
| storing in a second volume a biocompatible polymer having a multi-phase mixture with a predetermined controlled release of selected pharmaceutical substance to modulate soft tissue response to the polymer (704) |
| mixing the biocompatible cross-linker and polymer into a mixture (706) |
| injecting the mixture into a patient and during or after injection, cross-linking the polymer in the patient (708) |

FIG. 5

| Forming a cross-linked filler composition having a biocompatible, biodegradable, nontoxic properties, the filler composition having a predetermined radiolucency greater than silicone or saline radiolucency (802) |
|---|
| Injecting the mixture as separate phases into the body and mixing the mixture during the injection process to cause cross-linking of the multiphase mixture (803) |
| Introducing the filler composition into a shell or an envelope of a soft tissue human implant prior to or during implantation of the shell or envelope into a lumen in a human body (804) |
| Cross-linking the filler composition, and the cross linking reaction occurs outside the shell/envelope or in-situ inside the shell/envelope (810) |

FIG. 6

```
┌─────────────────────────────────────┐
│   Mix HA and PVA in water at 45C    │
│          for 3hrs (10)              │
└─────────────────────────────────────┘
                  │
┌─────────────────────────────────────┐
│    Freeze at -20C for 20hrs (12)    │
└─────────────────────────────────────┘
                  │
┌─────────────────────────────────────┐
│     Sit at Room Temp for 8hrs (14)  │
└─────────────────────────────────────┘
                  │
┌─────────────────────────────────────┐
│      Sterilize and Package (16)     │
└─────────────────────────────────────┘
```

FIG. 7A

Mix HA and PVA in water (50)

Sterilize Mixture (52)

Perform Multiple Freeze/Thaw Cycles (54)

Thaw at Room Temperature and then Package (56)

FIG. 7C

```
┌─────────────────────────────────┐
│  Mix HA and PVA in water at 45C │
│        for 3hrs (70)            │
└─────────────────────────────────┘
                │
                ▼
┌─────────────────────────────────┐
│      Sterilize Mixture (72)     │
└─────────────────────────────────┘
                │
                ▼
┌─────────────────────────────────┐
│    Multiple Freeze/Thaw Cycles  │
│              (74)               │
└─────────────────────────────────┘
                │
                ▼
┌─────────────────────────────────┐
│   Sit at Room Temp for 8hrs (76)│
└─────────────────────────────────┘
                │
                ▼
┌─────────────────────────────────┐
│          Package (78)           │
└─────────────────────────────────┘
```

FIG. 7D

Mix HA and PVA in water (80)

Sterilize Mixture and cross-linking with eBeam (82)

Optionally perform one or more Freeze/Thaw Cycles (84)

Package (86)

FIG. 7E

BODY AUGMENTATION DEVICE

This application is a continuation-in-part of application Ser. No. 14/255,967 filed May 1, 2014, which claims priority to Provisional application Ser. 61/722,221 filed Nov. 4, 2012, and PCT Application Serial PCT/VN2013/000001 filed Apr. 12, 2013, PCT/VN2013/000002 filed Apr. 12, 2013, PCT/VN2013/000003 filed on Apr. 12, 2013, PCT/VN2013/000004 filed Apr. 12, 2013, and PCT/VN2012/000008 filed Dec. 17, 2012, the contents of which are incorporated by reference.

BACKGROUND

The present invention relates to biodegradable hyaluronic acid filler compositions for soft tissue implants and body augmentation such as dermal fillers or breast, butt or body implants.

Everyone wants healthy and younger-looking skin. Having smoothskin and youthful appearance can make a person appear years younger, feel beautiful and more self-assured. Injectable dermal implants are a popular solution to correct a wide variety of facial contour defects that are congenital or as a result of serious accidents. The injectable dermal implants are very effective in cosmetic surgery procedures such as lip augmentation and scar removal.

Generally, as the years take its tolls on the body, the cells that generate the connective tissues that makeup the scaffold of the body become less efficient, and cannot keep up with the daily repair processes. Thus, our skin loses resiliency, elasticity and from which onsets wrinkles. The gerontological process happens at seemingly exponential speed.

The concept of biocompatibility is moving from a "do-no-harm" mission (i.e., nontoxic, non-antigenic, non-mutagenic, etc.) to one of "doing-good," that is, encouraging positive healing responses. These new devices will promote the formation of normal healthy tissue as well as the integration of the device into adjacent tissue. In some contexts, biocompatibility can become a disruptive technology that can change therapeutic paradigms (e.g., drug-coated stents).

The required material properties are determined by the specific device application and the functional life of the device, which ranges from temporary use to permanent implant. Devices can be used in:

1. blood-contacting applications such as extracorporeal devices that remove and return blood from the body, devices that are inserted into a blood vessel, or devices that are permanently implanted.
2. soft-tissue device applications, such as soft-tissue augmentation;
3. orthopedic and dental applications for joint, bone, and tooth replacement and repair
4. specific organ applications (e.g., neural); and
5. scaffolds for tissue engineering for tissue and organ replacement.

Development of an injectable hydrogel for tissue repair or tissue regeneration presents considerable challenges. The gelation conditions for in vivo use are limited to a narrow range of physiologically acceptable temperatures, and the crosslinking must occur with no by-products in a sensitive aqueous environment. Reagents must be nontoxic reagents and tolerant of moist, oxygen-rich environments. Furthermore, gelation must occur at a sufficiently rapid rate for clinical use in an outpatient or operating suite setting, yet sufficiently slow that complete mixing occurs prior to gelation.

In a parallel trend, millions of women have undergone breast, butt or body augmentation and reconstruction in the past few decades. Most women choose augmentation to enhance the size and shape of one or both breast, butt or body parts for personal or aesthetic reasons. In contrast, women who undergo a reconstruction procedure want to reconstruct a breast, butt or body that has been removed, typically for health reasons, such as tumor removal. The reconstruction procedure may vary from a modified radical mastectomy (removal of the underlying muscle as well as the breast, butt or body), to a simple mastectomy (removal of one breast, butt or body), to a bilateral mastectomy (removal of breast, butt or body parts) or to a lumpectomy (removal of a portion of the breast, butt or body). In either augmentation or reconstruction, the modality intimates the surgical implantation of breast, butt or body prosthesis (implant).

Conventional implants for treating breast, butt or body augmentation or reconstruction include a shell or envelope that is filled with a filler composition, for example, silicone gel, saline solution, or other suitable filler. It is desirable that the filler have lubricating properties to prevent shell abrasion, remain stable over long periods of time, be non-carcinogenic and non-toxic, and have physical properties to prevent skin wrinkling, capsular contracture formation, and implant palpability.

While breast, butt or body implants containing silicone-gel as a filler are widely used for breast, butt or body augmentation or reconstruction, a variety of potential disadvantages have been recognized with respect to the stabilization of the implants and the immune system. First, the silicone gel-filled implants have a tendency to leak. In 1992, the FDA issued a voluntary moratorium on silicone gel-filled implants due to public health concerns regarding the potential link between leaking silicone gel-filled implants and autoimmune diseases. To date, the long term effect of silicone-gel on the immune system is still unknown. Second, the leaking of the implants necessitates the need for additional surgeries for removal or repair of the implants. Third, the silicone-gel as a filling material has a greater density than saline or natural tissues which may cause recipients back pain. Fourth, silicone is a permanent filler composition and when it leaks, it can travel though out the body and can cause unwanted hard nodular formations if left untreated. Lastly, the silicone-gel implant although currently the state of the art, it does not mimic the touch and feel of a real breast, butt or body. It offers a more realistic feel than saline as a filler material.

Many plastic surgeons turned to saline as an alternative replacement for silicone-gel. Several implants which use saline are known and were found to be advantageous over silicone-gel for several reasons. Saline has a lower density than silicone-gel causing less strain on recipients' backs. In addition, if the implant leaks, the saline solution is biocompatible providing a more tolerated and safer implant than those containing silicone-gel.

However, while the saline implant offer significant advantages over the silicone-gel implant, various problems have been encountered. Implants using saline are disadvantageous in that they frequently result in capsular contraction, a phenomenon where the body forms a lining of fibrous tissue encapsulating the breast, butt or body implant and the resulting capsule tightens and squeezes the implant. Symptoms range from mild firmness and mild discomfort to severe pain, distorted shape, palpability of the implant, and/or movement of the implant. Additional surgery may be needed in cases where pain and/or firmness are severe. This surgery ranges from removal of the implant capsule tissue to removal and possibly replacement of the implant itself. There is no guarantee that capsular contracture will not occur after these additional surgeries.

Saline implants may have to be removed and replaced periodically for other reasons—they fracture or they deflate. Saline, because it is less viscous than silicone-gel, settles in the bottom portion of the implant when the recipient is upright. This leaves the upper portion of the implant prone to excessive folding or wrinkling, causing stress fracturing of the shell at the fold points. Furthermore, the saline-filled implants have a tendency to drain gradually in about ten years. Barring any deflation or rupture complications, saline as a filler for breast, butt or body implants produces an unnatural feel and look to the implant.

U.S. Pat. No. 6,881,226 discloses a breast, butt or body implant having at least an outer shell which is composed of a resorbable material. The implant, which can be formed entirely of bioresorbable material such as collagen foam, is sized and shaped to replace excised tissue. The implant supports surrounding tissue upon implantation, while allowing for in-growth of fibrous tissue to replace the implant. According to various alternative embodiments, the implant is elastically compressible, or can be formed from self-expanding foam or sponges, and can be implanted through a cannula or by injection, as well as by open procedures. The implant can carry therapeutic and diagnostic substances.

In response to the failures of saline and silicone-gel implants, there have been a number of attempts to make a prosthesis filled with a non-toxic filler that that mimics the shape and feel of a natural breast, butt or body provided by silicone-gel yet is safe to the immune system like saline. Other attempts to provide a safe filler material include polyethylene glycol. However, the triglyceride oil or honey fails to provide an implant that is aesthetically pleasing and also duplicates the touch and feel of a natural breast, butt or body due to the low viscosity of the fillers. Due to the limited options and the inadequacy of current fillers to achieve the desired results, there is a need for safe and efficacious fillers.

SUMMARY

In one aspect, systems and methods are disclosed for body augmentation by mixing hyaluronic acid (HA) with polyvinyl alcohol (PVA) to form an HA-PVA hydrogel; and exposing the HA-PVA hydrogel to one or more freeze-thaw cycles or to an amount of radiation effective to crosslink the HA to the PVA to crosslink the HA to the PVA.

In another aspect, systems and methods are disclosed for cosmetic augmentation by storing a biocompatible polymer; cross-linking the biocompatible polymer by applying energy; and augmenting soft tissue with the biocompatible cross-linked polymer.

In yet another aspect, systems and methods are disclosed for making a cross-linked hydrogel by mixing hyaluronic acid (HA) with polyvinyl alcohol (PVA) in a container to form an HA-PVA hydrogel; and exposing the HA-PVA hydrogel to an amount of energy effective to crosslink the HA and the PVA and to sterilize the container content.

In a further aspect, systems and methods are disclosed for cosmetic augmentation by storing a non-toxic biocompatible cross-linker; storing a biocompatible polymer having a multi-phase mixture with a predetermined controlled release of selected pharmaceutical substance to modulate soft tissue response to the polymer; mixing the biocompatible cross-linker and polymer into a mixture; injecting the mixture into a patient and during or after injection, cross-linking the polymer in the patient; and augmenting soft tissue with the biocompatible cross-linked polymer.

In another aspect, systems and methods are disclosed for making a cross-linked hydrogel by mixing hyaluronic acid (HA) with polyvinyl alcohol (PVA) in a container to form an HA-PVA hydrogel; sterilizing the HA-PVA hydrogel at a temperature between 200-300 deg C.; and exposing the HA-PVA hydrogel to one or more freeze-thaw cycles to crosslink the HA to the PVA.

In another aspect, systems and methods are disclosed for making a cross-linked hydrogel by mixing hyaluronic acid (HA) with polyvinyl alcohol (PVA) in a container to form an HA-PVA hydrogel; and exposing the HA-PVA hydrogel to an amount of radiation effective to crosslink the HA to the PVA and to sterilize the container content.

In another aspect, systems and methods are disclosed for cosmetic augmentation by forming a biocompatible cross-linked polymer having a multi-phase mixture with a predetermined controlled release of selected pharmaceutical substance to modulate soft tissue response to the polymer; injecting the mixture into a patient and during or after injection, cross-linking the polymer in the patient; and augmenting soft tissue with the biocompatible cross-linked polymer.

In another aspect, systems and methods are disclosed for breast, butt or body implants by forming a biocompatible cross-linked polymer having a multi-phase mixture with a predetermined controlled release of selected pharmaceutical substance to modulate soft tissue response to the polymer; injecting the mixture into a patient and during or after injection, cross-linking the polymer in the patient; filling a semi-permeable shell with the pharmaceutical substance; and augmenting soft tissue with the biocompatible cross-linked polymer.

Advantages of the system may include one or more of the following. The flow properties are tailored for injection through a small bore needle. The system has greater flexibility to control physical properties of the final gel. The final gel could be tailored to have greater cohesive strength which will resist migration to another anatomical space. The final gel durometer could be tailored to be more natural, similar in feel and appearance to the surrounding tissue. The final gel could be tailored to have properties similar to surround tissue. The longevity of the final gel could be tailored to meet various anatomical location requirements (longer biodegradation or shorter depending on anatomical location). The final gel physical properties stay constant over the life time of the material.

Other advantages of various embodiments can include one or more of the following. A natural feel is achieved through viscoelastic harmony of properties between the existing tissue and the implant. This is achieved by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in body augmentaton applications. Other advantages and features include: longevity without touch up, hyper-volumic degradation, anatomic compliant and iso-osmotic controlled, among others. Because the HA-PVA hydrogel can be manufactured to be mechanically strong, or to possess various levels of strength among other physical properties depending upon the weight percentage of the HA-PVA starting material with respect to other constituents in solution, freeze time, the number of freeze/thaw cycles, and the freeze temperature. The end product hydrogel also has a high water content which provides desirable properties in numerous applications and which prevents the denaturing of additives. The hydrogel tissue replacement construct is especially useful in surgical and other medical applications as an artificial material for replacing and reconstructing soft tissues in humans and other mammals. One major use is in breast augmentation or buttock augmentation or other aesthetic medical applications. Soft tissue body parts which can be replaced or reconstructed by the hydrogel include, but are not limited to, vascular grafts, heart valves, esophageal tissue, skin, corneal tissue, ureternal stents, nerve bridge, wound covering cartilage, meniscus, and tendon. The hydrogel may be formed as an implantable articulating surface for a load bearing joint, whereby the articulating surface may be fixed to bone with screws, sutures, or bioglue such as a collagenglue. Furthermore, the hydrogel may also serve as a cartilage replacement for anatomical structures including, but not limited to an ear or nose. The inventive hydrogel may also serve as a tissue expander. Additionally, the inventive hydrogel may be suitable for an implantable drug delivery device. In that application, the rate of drug delivery to tissue will depend upon hydrogel pore size and degree of intermolecular meshing resulting from the freeze/thaw cycles. The rate of drug delivery increases with the number of pores and decreases with an increasing degree of intermolecular meshing from an increased number of freeze/thaw cycles. The hydrogel is suitable for vascular grafts and heart valve replacements, because the hydrogel is thromboresistant, and because of the particular mechanical and physiological requirements of vascular grafts when implanted into the body. The hydrogel may also be used for contact lenses, as a covering for wounds such as burns and abrasions, and in other applications wherein a mechanically strong material is preferred.

BRIEF DESCRIPTION OF THE DRAWINGS

FIG. 5 shows an exemplary process to inject and cross-link materials at the same time.

FIG. 6 shows another exemplary process to inject and cross-link materials at the same time.

FIGS. 7A-7E show exemplary hydrogel fabrication processes that can produce large volume of gels for minimally invasive body augmentation.

FIG. 8A shows exemplary HA-PVA bonding configurations with ester bonding, while

DESCRIPTION

Figure 1:
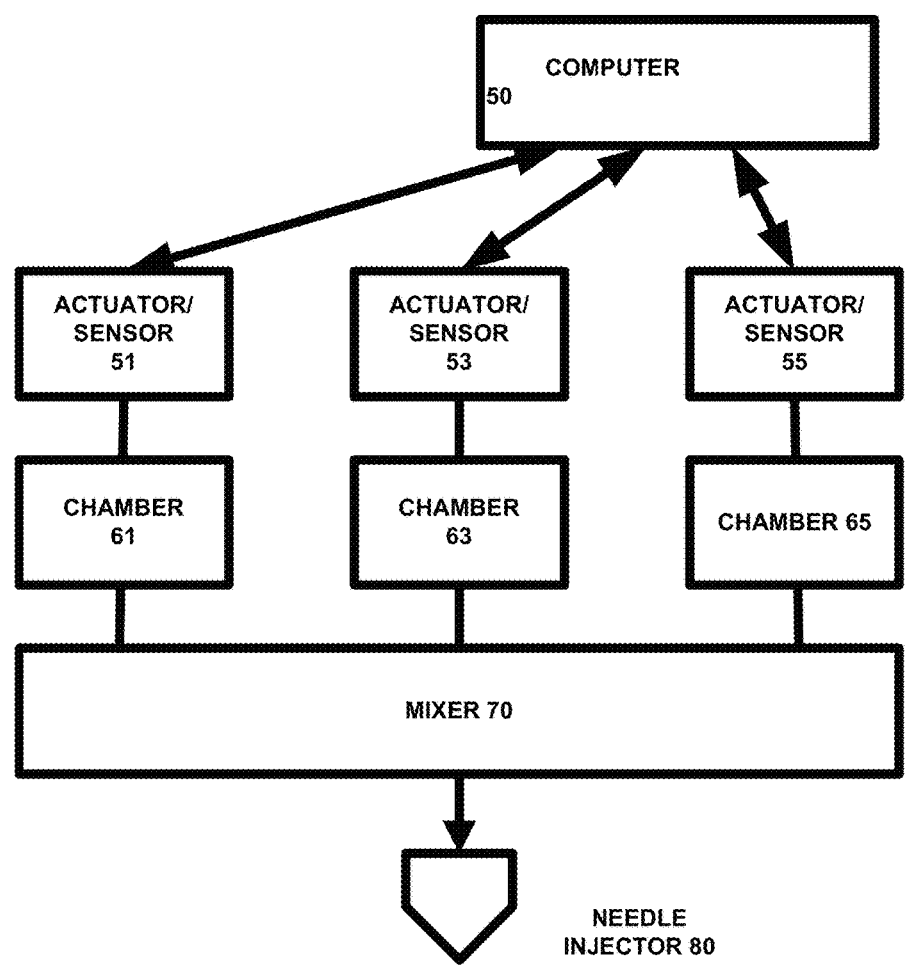
FIG. 1 shows an exemplary block diagram of a computer controlled hyaluronic acid (HA) injector system that cross-links the HA while the drug is injected into the body.

FIG. 1 shows an exemplary block diagram of a hyaluronic acid (HA) injector system that cross-links the HA while the drug is injected into the body. As shown therein, a triple cartridge with parallel container search housing one of three flowable components to be mixed when desired in a static mixer and which terminates in an outlet tip from which the components mixed by the static mixer are expelled. The static mixer may be separable from and attached to the containers or chambers in a manner known per se. The containers, usually made of a plastics material, are joined by a bridge defining an outlet in which the two components are separated by an internal dividing wall to maintain the components separate and unmixed until they reach inlet of the static mixer for mixing therein. In a conventional manner, the static mixer, again usually of a plastics material, comprises a static mixer element housed in an elongate member extending from attachment to the outlet to outlet tip. Also the static mixer element comprises an axially extending serial plurality of alternating oppositely oriented helically twisted mixer blades which act in concert to efficiently and thoroughly mix the separate components as they flow through the static mixer 6 from the outlet to the outlet tip. Pistons or motorized actuators are operated simultaneously by a suitable mechanism (not shown) with the cartridge being retained by the back plate, to dispense the components simultaneously from the containers through the outlet and static mixer to the outlet tip. In this embodiment, the actuators are controlled by a computer for precise mixing and delivery as desired. Moreover, a plurality of outlets can be provided so that a plurality of patient areas can be injected in parallel.

The most widely used material for scaffolding and tissue engineering is hyaluronic acid. This material is a major constituent of the extracellular matrix (ECM), and is the only non-sulfatedglycosaminoglycan (GAG). This poly-anionic molecule is ubiquitous, biocompatible, biodegradable, and performs many important biological functions.

Some of these functions are:
stabilizing and organizing the ECM
regulating cell adhesion
motility,
mediating cell proliferation
and differentiation.

The molecular weight of HA can get very high, as high as a few million Daltons. This fact along with its biocompatibility nature makes HA is an ideal scaffolding material and tissue engineering material only if did not biodegrade so fast. How quick it biodegrades depends on the specie and the anatomical location. The half-life degradation range of HA is between 1 day to several days. Through chemistry, the biodegradation of HA may be interfered with or slowed down through cross-linking. Conventional chemistry to cross-link HA yields cross-link HA molecule that has non-Newtonian properties making it very difficult to deliver it to the intended target. As discussed earlier in the background section, the best method to use HA in an augmentation application is to cross-link it in-situ inside the body at the target site.

There are several methods to cross-link HA in-situ, and they vary in their detrimental impacts on the neighboring tissue in-vivo. Four in-situ methods are summarized here, and the biocompatibility tests to characterize the impact of the process steps of these cross-linking methods showed that they were able to meet the requirements for the biocompatibility and that the cross-linking reactions and their by-products were not detrimental to the respective surrounding tissues:

1. A 3-Thiopropanoyl hydrazide HA (HA-DTPH) derivative cross-linked with polyethylene glycol diacrylate is an efficient reaction that complete in approximately 9 minutes at a molar ratio of 2 to 1. In biocompatibility tests conducted to characterize the in-situ process, there was no significant adverse event observed or recorded. The figure below shows a chemical structure of an a, b unsaturated esters and amides of PEG cross-linked with thiolated HA.

nent making this product functional. The hyaluronan strands are extruded from cation-exchanged sodium hyaluronate (1.6 MDa) were cross-linked in glutaraldehyde aqueous solution. The strand surfaces were then remodeled by attachment of poly-D- and poly-L-lysine. The polypeptide-resurfaced hyaluronan strands showed good biocompatibility and promoted cellular adhesion.

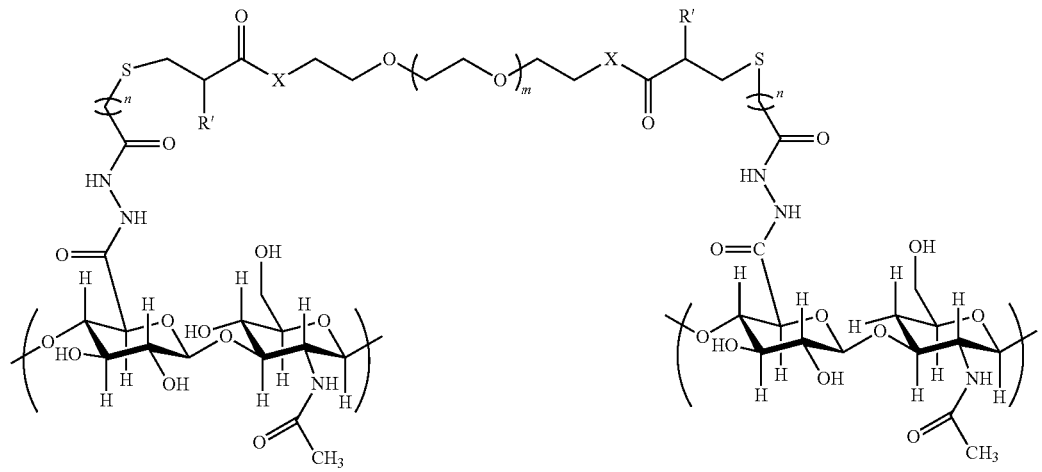

2. Other hydrazide methods include using the hydrazide chemistry described above for hydrogels that have been prepared using bishydrazide, trishydrazide, and polyvalent hydrazide compounds as cross-linkers. By adjusting the reaction conditions and the molar ratios of the reagents, gels with physicochemical properties ranging from soft-pourable gels to more mechanically-rigid and brittle gels could be obtained. HA-ADH can be cross-linked using commercially-available small molecule homobifunctional cross-linkers, shown the figure below.

4. Photo cross-linking is another method to cross-link HA using a methacrylate derivative of hyaluronan was synthesized by the esterification of the hydroxyls with excess methacrylic anhydride, as described above for hyaluronan butyrate. This derivative was photo-cross-linked to form a stable hydrogel using ethyl eosin in 1-vinyl-2-pyrrolidone and triethanolamine as an initiator under argon ion laser irradiation at 514 nm. The use of in situ photo-polymerization of an hyaluronan derivative, which results in the formation of a cohesive gel enveloping the injured tissue, may provide isolation

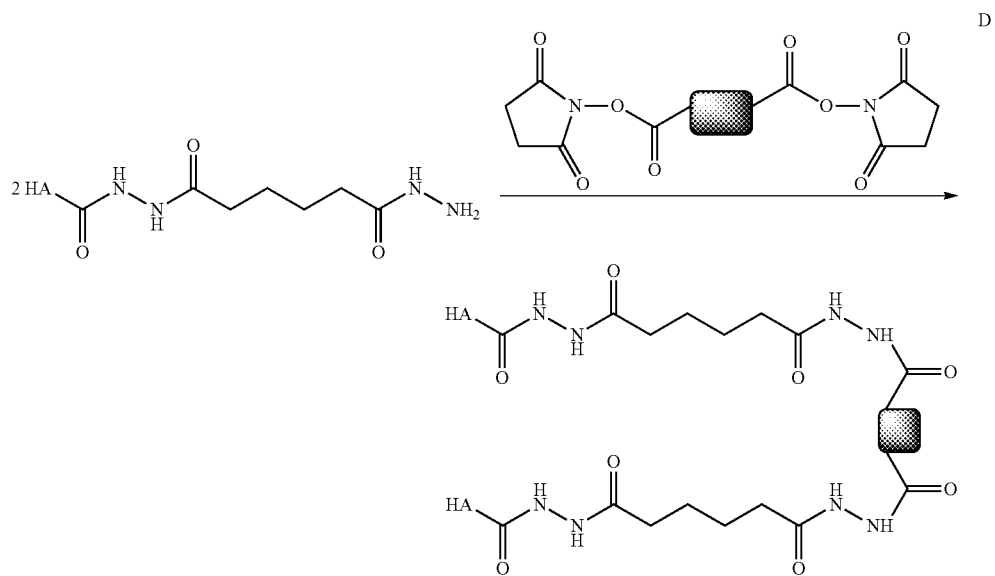

3. HA may be cross-linked first by ex-situ using the glutaraldehyde method. Ion exchange is key compofrom surrounding organs and thus prevent the formation of adhesions. A preliminary cell encapsulation study was successfully performed with islets of Langerhans to develop a bio-artificial source of insulin.

Preferably, the cross linker is non-toxic and safe for human use. In one embodiment, the cross linker improves the resistance of HA in the human body to mechanical degradation by contacting at least a portion of a HA with an effective amount of a crosslinking reagent. In one embodiment, a method of curtailing the progressive mechanical degradation of HA by enhancing the body's own efforts to stabilize the HA material by increasing collagen crosslinks. In this embodiment, this mechanical degradation may be in response to physiologic levels of repetitive loading. The crosslinking reagent is not particularly limited. Any crosslinking reagent known to be substantially non-cytotoxic and to be an effective cross-linker of collagenous material may be used. The crosslinking reagent is required to be substantially non-cytotoxic in order to facilitate direct contact of the crosslinking agent to tissues in the living human body. Preferably, the crosslinking reagent exhibits substantially less cytotoxicity compared to common aldehyde fixation agents. More preferably, a non-cytotoxic crosslinking reagent is used. Appropriate cytotoxicity testing will be used to verify the minimal cytotoxicity of candidate crosslinking reagents prior to use in humans. Tissue specific in vitro tests of cytotoxicity, of the standard form applied to mouse connective tissue (F895-84 (2001)e1 Standard Test Method for Agar Diffusion Cell Culture Screening for Cytotoxicity), or Chinese Hamster Ovaries (ASTM E1262-88 (1996) Standard Guide for Performance of the Chinese Hamster Ovary Cell/Hypoxanthine Guanine Phosphoribosyl Transferase Gene Mutation Assay) preferably utilizing cell lines from tissues approximating the fibrous and gelatinous tissues of the intervertebral disc, should be conducted to evaluate the level of toxicity of any specific combination of crosslinking reagents known to have minimal cytotoxicity. These in vitro tests should similarly be followed by in vivo animal tests prior to use in humans.

The crosslinking reagent includes at least one crosslinking agent. The crosslinking agent chosen in accordance with the present invention is an effective cross-linker of collagenous material. When used in a cross-linking reagent, an effective crosslinker is one that increases the number of crosslinks in the HA when the crosslinker is brought into contact with a portion of the HA. An effective crosslinker improves the fatigue resistance of the treated HA, reduces material property degradation resulting from repetitive physiologic loading, or reduces the increase of viscoelastic properties of the treated tissue due to fatigue loading. Likewise, an effective crosslinker may reduce the decrease in elastic-plastic properties due to fatigue loading of the treated tissue. In one embodiment of the present invention, the crosslinking agent can be Genipin, a substantially non-toxic, naturally occurring crosslinking agent. Genipin is obtained from its parent compound, geniposide, which may be isolated from the fruits of Gardenia jasminoides. Genipin may be obtained commercially from Challenge Bioproducts Co., Ltd., 7 Alley 25, Lane 63, TzuChiang St. 404 Taichung Taiwan R.O.C., Tel 886-4-3600852. In another embodiment of the present invention, the crosslinking agent is a bioflavonoid, and more specifically, the bioflavonoid is proanthrocyanidin. A mixture containing proanthrocyanidin can be obtained as MegaNatural™ Gold from Polyphenolics, Inc, 22004 Rd. 24, Medera, Calif. 93638, Tel 559-637-5961. More than one crosslinking agent may be used. Appropriate cross-linking reagents will also include sugars such as ribose or threose, lysyl oxidase (LO) enzyme, an LO promoter, an epoxy and a carbodiimide. These agents have been used in Patent Application 20040253219 to stabilize discs in scoliotic spines by increasing collagen crosslinks, the content of which is incorporated by reference.

The crosslinking reagent may include a carrier medium in addition to the crosslinking agent. The crosslinking agent may be dissolved or suspended in the carrier medium to form the crosslinking reagent. In one embodiment, a crosslinking agent is dissolved in a non-cytotoxic and biocompatible carrier medium. The carrier medium is required to be substantially non-cytotoxic in order to mediate the contact of the crosslinking agent to tissues in the living human body without substantial damage to the tissue or surrounding tissue. Preferably, the carrier medium chosen is water, and more preferably, a saline solution. Preferably, the pH of the carrier medium is adjusted to be the same or similar to the tissue environment. Even more preferably, the carrier medium is buffered. In one embodiment of the present invention, the carrier medium is a phosphate buffered saline (PBS).

When the crosslinking agent is dissolved in a carrier medium, the concentration of the crosslinking agent in the carrier medium is not particularly limited. The concentration may be in any amount effective to increase the crosslinking of the tissue while at the same time remaining substantially noncytotoxic.

In accordance with the present invention, the crosslinking reagent is brought into contact with a portion of a collagenous tissue. As used herein, collagenous tissue is defined to be a structural or load supporting tissue in the body comprised of a substantial amount of collagen. Examples would include intervertebral disc, articular cartilage, ligament, tendon, bone, and skin. In general, the portion of the collagenous tissue to be brought into contact with the crosslinking reagent is the portion of the tissue that is subject to loading. Further, where at least some degradation of the collagenous tissue has occurred, the portion of the tissue to be contacted with the crosslinking reagent is at least the portion of the tissue that has been degraded. Preferably, the entire portion that is subject to loading or the entire portion that is degraded is contacted with the crosslinking reagent. Further, the tissue adjacent the portion of collagenous tissue subject to the loading may also be contacted with the crosslinking reagent.

The selected portion of the collagenous tissue must be contacted with an effective amount of the non-toxic crosslinking reagent. An "effective amount" is an amount of crosslinking reagent sufficient to have a mechanical effect on the portion of the tissue treated. Specifically, an "effective amount" of the crosslinking reagent is an amount sufficient to improve the fatigue resistance of the treated tissue, reduce material property degradation resulting from repetitive physiologic loading, or reduce the increase of viscoelastic properties of the treated tissue due to fatigue loading, or reduce the decrease of elastic-plastic properties of the treated tissue due to fatigue loading.

The method of the present invention includes contacting at least a portion of the HA or patient tissue with an effective amount of the crosslinking reagent. The contact may be affected in a number of ways. Preferably, the contacting of HA or collagenous tissue is affected by a means for minimally invasive delivery of the non-cytotoxic crosslinking reagent. Preferably, the contact between the tissue and the crosslinking reagent is effected by injections directly into the select tissue using a needle. Preferably, the contact between the tissue and the crosslinking reagent is effected by injections from a single or minimum number of injection locations. Preferably, an amount of crosslinking solution is injected directly into the targeted tissue using a needle and a syringe. Preferably, a sufficient number of injections are made along the portion of the tissue to be treated so that complete coverage of the portion of the collagenous tissue to be treated is achieved.

Alternatively, contact between the tissue and the cross-linking reagent is affected by placement of a time-release delivery system or temperature release deliver system directly into or onto the target tissue. One time-released delivery system that may be used is a treated membrane or patch. A reagent-containing patch may be rolled into a cylinder and inserted percutaneously through a cannula to the tissue sight, unrolled and using a biological adhesive or resorbable fixation device (sutures or tacks) be attached to the periphery of the targeted tissue.

Another time-released delivery system that may be used is a gel or ointment. A gel or ointment is a degradable, viscous carrier that may be applied to the exterior of the targeted tissue. Contact also may be effected by soaking or spraying, such as intra-capsular soaking or spraying, in which an amount of crosslinking solutions could be injected into a capsular or synovial pouch.

It should be noted that the methods and compositions treated herein are not required to permanently improve the resistance of collagenous tissues in the human body to mechanical degradation. The contacting may be repeated periodically to maintain the increased resistance to fatigue. For some treatment, the time between contacting is estimated to correspond to approximately 1 year for some individuals. Therefore, with either a single treatment or with repeated injections/treatments, the method of the present invention minimizes mechanical degradation of the collagenous tissue over an extended period of time.

Bioflavinoids and geniposides can be effective cross-linkers with minimal cytotoxicity. Similarly, sugar (e.g., ribose or threose) solutions have been shown to increase the number of non-enzymatic glycation produced crosslinks (naturally produced crosslinks, pentosidine is one example). Lysyl oxidase is the naturally produced enzyme involved in the formation of immature and mature endogenous (naturally occurring) collagen crosslinks. The method used to increase the crosslinking HA or surrounding tissue may include directly contacting living human tissue with appropriate concentrations of minimally-cytotoxic crosslinking reagents such as genipin (a geniposide) or proanthocyanidin (a bioflavinoid) or a sugar such as ribose or threose, or lysyl oxidase (LO) enzyme, or a LO promoter, or an epoxy or a carbodiimide.

A treatment method according to this embodiment incorporates a means for minimally invasive delivery of the non-cytotoxic crosslinking reagent such as placement of a time-release delivery system such as an imbedded pellet or time release capsule, or a treated membrane or patch directly into or onto the target tissue. Additional, guidable, arthroscopic-types of devices may be developed to facilitate application of the reagents to appropriate areas on the intervertebral discs or adjacent bony, capsular or ligamentous tissues.

A major limitation of most scaffold materials used for tissue engineering is the need for surgical implantation. For many clinical uses such as anatomical aesthetic augmentation of the body such as various areas on the face, the breast, butt or body, and the buttock, injectable in situ cross-linkable hydrogels such as hyaluronic acid (HA) would be strongly preferred for three main reasons.

1. In-Situ Reaction, an injectable material could be formed into any desired shape at the site of injury. Because the initial materials could be sol gels or moldable putties, the systems may be positioned in complex shapes and then subsequently cross-linked to conform to the required dimensions.

2. Mechanical Attachment, the cross-linkable polymer mixture would adhere to the tissue during gel formation, and the resulting mechanical interlocking that would arise from surface micro-roughness would strengthen the tissue-hydrogel interface.

3. Minimal Invasiveness, of an in situ cross-linkable hydrogel could be accomplished by injection or laparoscopic methods, thereby minimizing the invasiveness of the procedure. For many clinical uses such as anatomical aesthetic augmentation of the body such as various areas on the face, the breast, butt or body, and the buttock, injectable in situ cross-linkable hydrogels such as hyaluronic acid (HA) would be strongly preferred for three main reasons.

Figure 2:
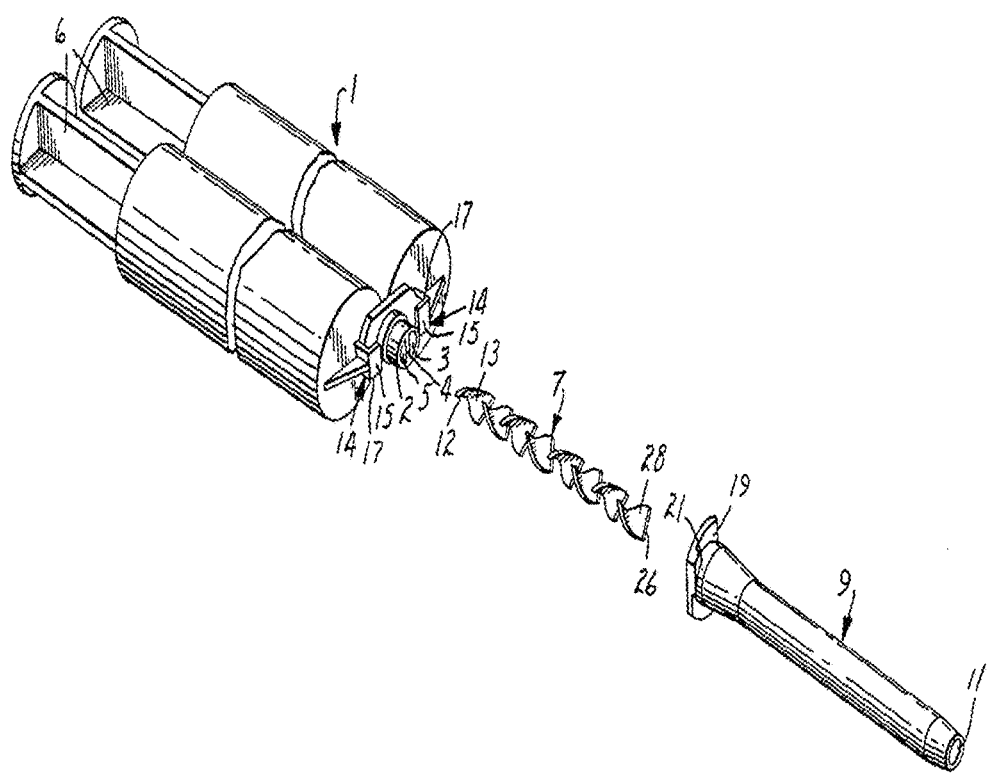
FIGS. 2-3 shows an exemplary manual hyaluronic acid (HA) injector system that cross-links the HA while the drug is injected into the body.

Referring now to FIG. 2, there is shown an exploded view in perspective of a static mixing device for forming cross-linked HA as it is injected into the patient. Although illustrated as a dual chamber device, syringe 1 has two or three parallel internal chambers, each of which is intended to be filled with a cross-linked material such as DVS, a filler material such as hyaluronic acid, and a catalyst such as sodium bicarbonate solute. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will rapidly polymerize following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

In one embodiment, maximum efficiency of mixing is obtained by insuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means described in more detail below, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

Syringe 1, exit nozzle 2, exit passages 3 and 5, barrier 4, plungers 6, static mixing element 7, exit conduit 9, inlet edge 12, first mixing blade 13, bayonet locking tabs 14, and locking prongs 15 are as in FIG. 1. Static mixing element 7 is rotationally aligned within exit conduit 9 by one or more guides proximate the outlet end of exit conduit 9. Guides 24 and 25 are small inward projections in the bore of exit conduit 9, and have a "fish mouth" appearance when viewed in perspective. When viewed in isolation, locking guides 24 and 25 each resemble the nib of a fountain pen.

When static mixing element 7 is inserted into the inlet end of exit conduit 9, and pushed toward the outlet end of exit conduit 9, guides 24 and 25 serve to rotationally align static mixing element 7 within exit conduit 9. When leading edge 26 of the final mixing blade 28 of static mixing element 7 approaches the outlet end of exit conduit 9, guides 24 and 25 cause static mixing element 7 to rotate about its long axis until leading edge 26 abuts edge surface 24a of guide 24 or edge surface 25a of guide 25.

When a static mixing element is inserted sufficiently far into exit conduit 9 to strike cusp 33, the leading edge of the static mixing element is deflected by cusp 33 toward edge surface 24a or toward edge surface 24b, thereby providing the desired rotational alignment. Depending upon whether the static mixing element abuts against edge surface 24a or 24b of guide 24 (and against corresponding edge surface 25b or 25a of guide 25), the final orientation of the static mixing element will be in one of two positions, each of those positions being 180° of rotation apart from the other. Each position is equally acceptable as a means for optimizing the efficiency of the first blade of the static mixing element, since in either position the first mixing element will intersect the incoming streams of resin at an approximate right angle to the plane of contiguity between the incoming streams and subdivide the incoming streams equally.

Although FIG. 2 shows two chambers 4, one embodiment provides three chambers 4: a first chamber containing a cross-linking material such as DVS, a second chamber containing hyaluronic acid (HA), and a third chamber containing a catalyst such as sodium bicarbonate solution.

The inner content 6 of the implant is a composition that is composed mainly of hyaluronic acid. The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term. HA can also be defined as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein. More details on how to make the HA are discussed in commonly owned, co-pending application Ser. No. 13/353,316, filed Jan. 18, 2012, and entitled "INJECTABLE FILLER," the content of which is incorporated by reference.

Figure 3:
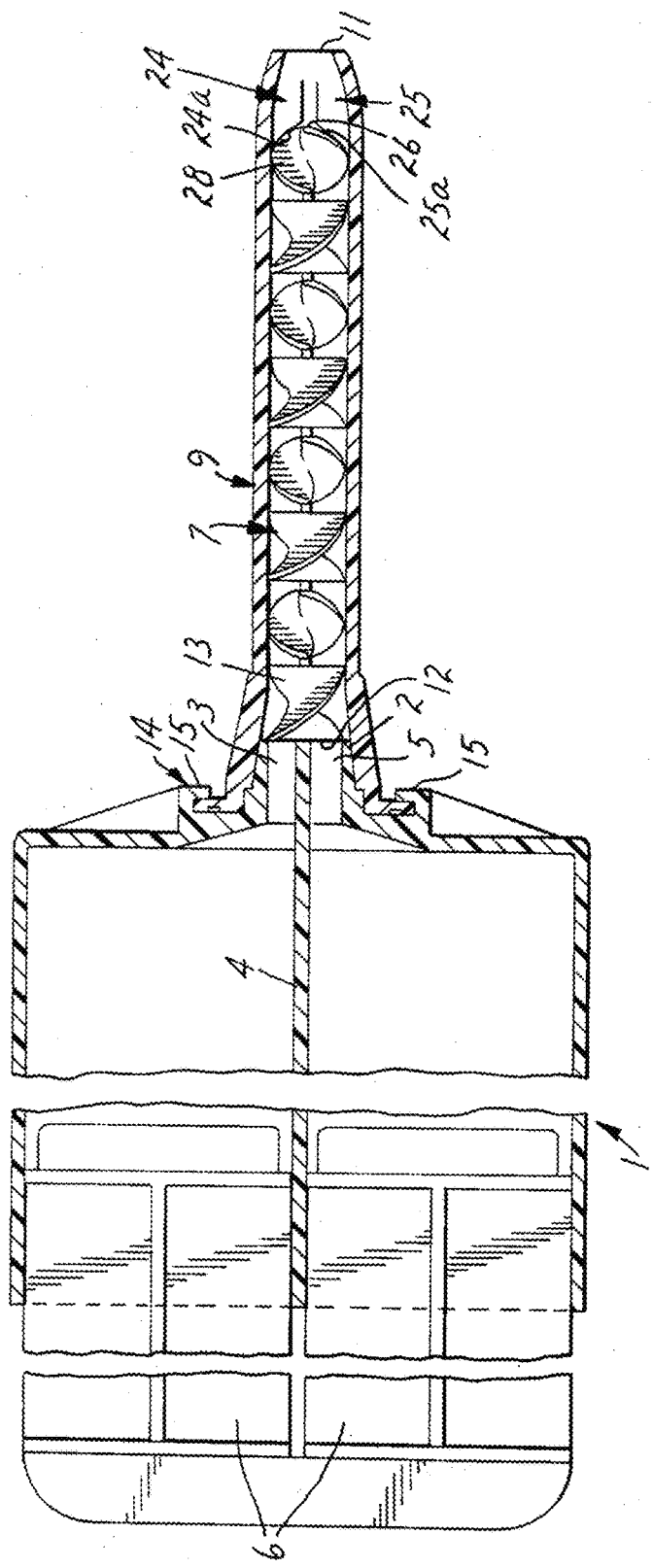
Figure 4:
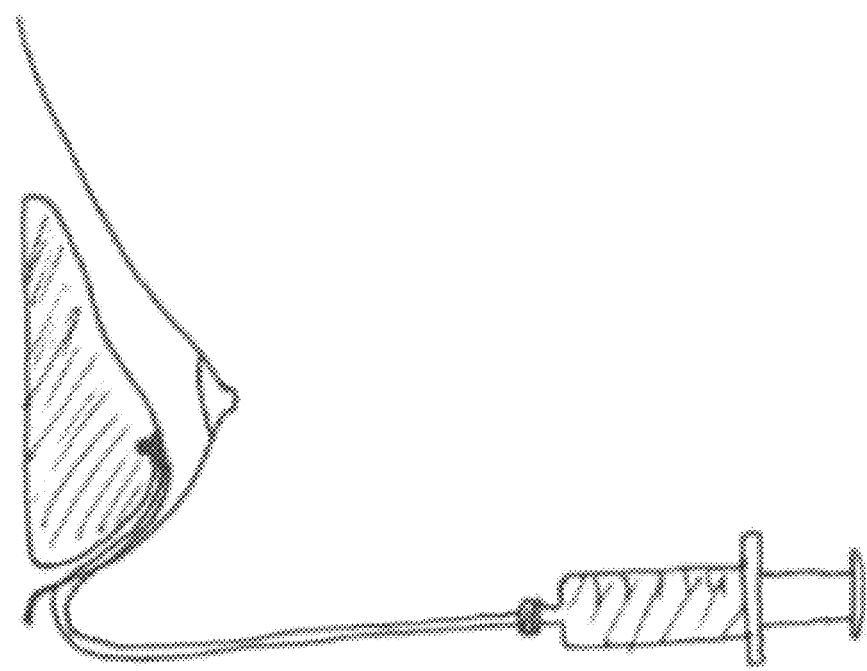
FIG. 4 shows an exemplary breast, butt or body implant delivery system.

The injectors of FIG. 1 or FIGS. 2-3 can be used to inject HA for dermal filling or for filling a breast, butt or body implant, as shown in FIG. 4.

FIG. 5 shows an exemplary process to inject and cross-link materials at the same time. The process includes storing a non-toxic biocompatible cross-linker in a first volume (702); storing in a second volume a biocompatible polymer having a multi-phase mixture with a predetermined controlled release of selected pharmaceutical substance to modulate soft tissue response to the polymer (704); mixing the biocompatible cross-linker and polymer into a mixture (706); and injecting the mixture into a patient and during or after injection, cross-linking the polymer in the patient (708).

FIG. 6 shows another exemplary process to inject and cross-link materials at the same time. The process includes forming a cross-linked filler composition having a biocompatible, biodegradable, nontoxic properties, the filler composition having a predetermined radiolucency greater than silicone or saline radiolucency (802). The process also injects the mixture as separate phases into the body and mixing the mixture during the injection process to cause cross-linking of the multiphase mixture (803). The filler composition with HA and cross linking materials is introduced into a shell or an envelope of a soft tissue human implant prior to or during implantation of the shell or envelope into a lumen in a human body (804). The cross-linking the filler composition occurs, and the cross linking reaction occurs outside the shell/envelope or in-situ inside the shell/envelope (810).

With certain HAs, the cross linking of the HA external to the shell can cause the cross-linked gel to become hardened and thus the HA may not be inserted into the shell easily with desired properties. A reversible cross-linking system can be used in one embodiment, where the cross links will be labile at extreme pH values, and at physiological pH, the cross-links become fixed. Two product streams can enter the shell, one is the product at an altered pH state and the other is the PBS, the neutralizer.

In the above processes, biocompatible reactants react in-situ to alter the physical properties a biocompatible polymer intended for said purpose from a deformable state to a non-deformable state. This polymer is a multi-phase mixture with a predetermined controlled release of selected pharmaceutical substances to modulate the response of the body to the polymer.

Gelling by either bioresponsive self-assembly or mixing of binary crosslinking systems, these technologies are useful in minimally invasive applications as well as drug delivery systems in which the sol-to-gel transition aids the formulation's performance. Moreover, not only does the chemical nature of the crosslinking moieties allow these systems to perform in situ, but they contribute dramatically to the mechanical properties of the hydrogel networks. For example, reversible crosslinks with finite lifetimes generate dynamic viscoelastic gels with time-dependent properties, whereas irreversible crosslinks form highly elastic networks.

The intrinsic properties of in situ forming gels add a new dimension of flexibility to large space augmentation such as that of the breast, butt or body and the buttock. While the silicone filled shell gives the feel and touch of native tissue, the long term health and legal complications associated of foreign body reaction and biocompatibility cannot be avoided. The over the lifetime of the implant, the fact that silicone fluid finding its way to the tissue on the outside of the shell is a kinetic eventuality. Saline filled shell has been a reluctant alternative because its feel and aesthetic affect are far from natural. The best of both worlds alternative might be found in a native material such as hyaluronic acids. The required properties might be best satisfied in an in situ crosslinked hyaluronic acid, or ex situ crosslinked hyaluronic acid or super high molecular weight linear (un-crosslinked) hyaluronic acids.

The following are examples of in situ crosslinking method for hyaluronic acids:

1. Hyaluronic acids, hydrazide and aldehyde:

Doubly crosslinked networks composed of HA microgels and crosslinked hydrogels with tunable is coelasticity in the relevant frequency range have been proposed for vocal fold healing. These partially monolithic and partially living materials feature divinylsulfone-crosslinked HA particles that have been oxidized with periodate to produce surface aldehyde functionalities.

A derivative of hyaluronic acid (HA), comprising the steps of:

1.1. forming an activated ester at a carboxylate of a glucuronic acid moiety of hyaluronic acid;

1.2. substituting at the carbonyl carbon of the activated ester formed in step 1.1

1.3. a side chain comprising a nucleophilic portion and a functional group portion; and 1.4. forming a cross-linked hydrogel from the functional group portion of the hyaluronic acid derivative in solution under physiological conditions wherein the forming of a cross-linked hydrogel is not by photo-cross-linking.

2. Hyaluronic acid, dextran by forming a hydrazine

Figure 9:
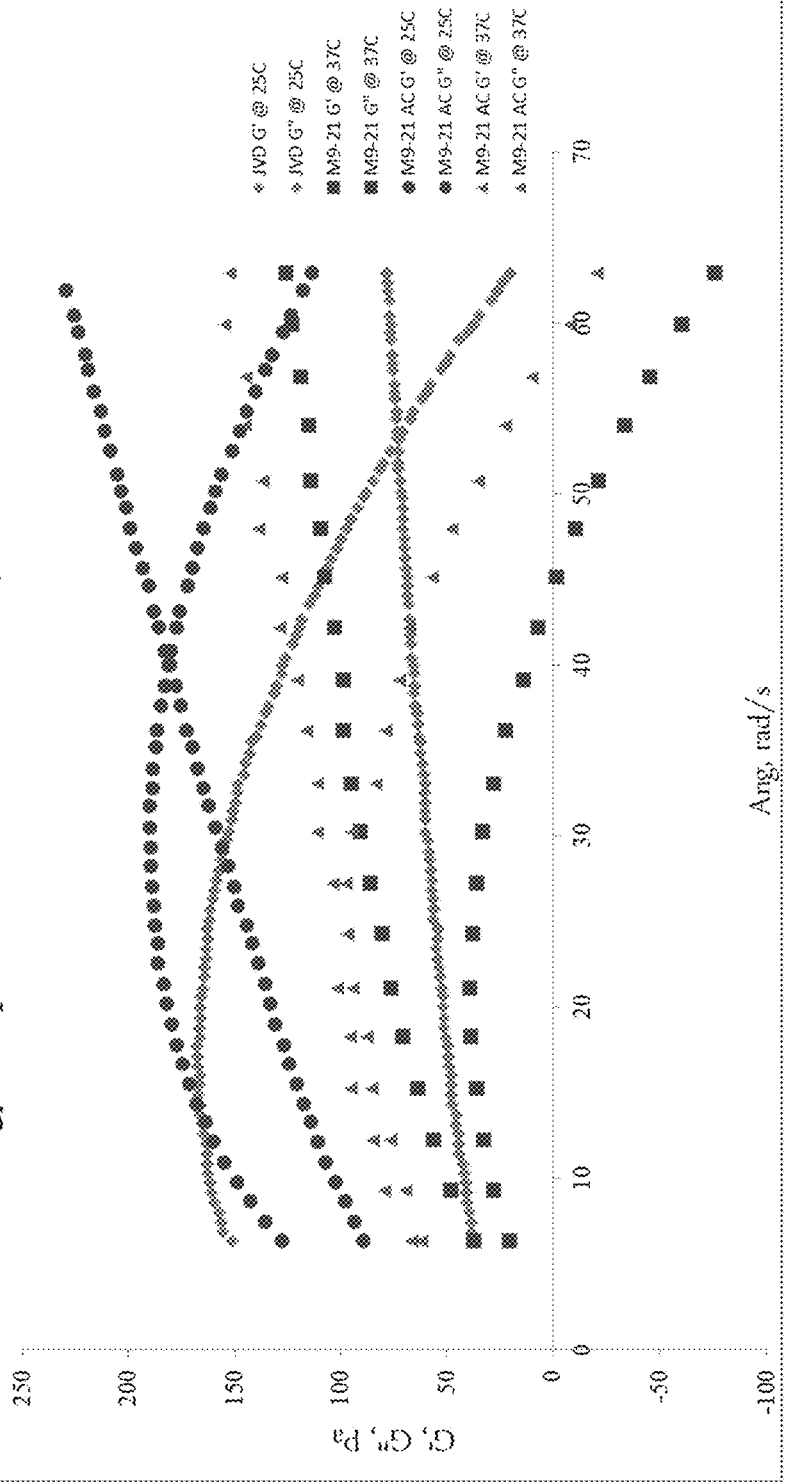
FIG. 9 show an exemplary comparison of one sample HA-PVA mixture to a commercial dermal filler.

3. Functionalization of hyaluronic acid (HA) with chemoselective groups enables in situ formation of HA-based materials in minimally invasive injectable manner. One embodiment of HA modification with such groups primarily rely on the use of a large excess of a reagent to introduce a unique reactive handle into HA and, therefore, are difficult to control. FIG. 9 shows another embodiment with a protective group strategy based on initial mild cleavage of a disulfide bond followed by elimination of the generated 2-thioethoxycarbonyl moiety ultimately affording free amine-type functionality, such as hydrazide, aminooxy, and carbazate. Specifically, new modifying homobifunctional reagents may be synthesized that contain a new divalent disulfide-based protecting group. Amidation of HA with these reagents gives rise to either one-end coupling product or to intra/intermolecular cross-linking of the HA chains. However, after subsequent treatment of the amidation reaction mixture with dithiothreitol (DTT), these cross-linkages are cleaved, ultimately exposing free amine-type groups. The same methodology was applied to graft serine residues to the HA backbone, which were subsequently oxidized into aldehyde groups. The strategy therefore encompasses a new approach for mild and highly controlled functionalization of HA with both nucleophilic and electrophilic chemoselective functionalities with the emphasis for the subsequent conjugation and in situ cross-linking. A series of new hydrogel materials were prepared by mixing the new HA-aldehyde derivative with different HA-nucleophile counterparts. Rheological properties of the formed hydrogels were determined and related to the structural characteristics of the gel networks. Human dermal fibroblasts remained viable while cultured with the hydrogels for 3 days, with no sign of cytotoxicity, suggesting that the gels described in this study are candidates for use as growth factors delivery vehicles for tissue engineering applications.

4. The gelation is attributed to the Schiff base reaction between amino and aldehyde groups of polysaccharide derivatives. In the current work, N-succinyl-chitosan (S-CS) and aldehyde hyaluronic acid (A-HA) were synthesized for preparation of the composite hydrogels.

5. Injectable hyaluronic acid (HA) hydrogels can be cross-linked via disulfide bond are synthesized using a thiol-disulfide exchange reaction. The production of small-molecule reaction product, pyridine-2-thione, allows the hydrogel formation process to be monitored quantitatively in real-time by UV spectroscopy. Rheological tests show that the hydrogels formed within minutes at 37° C. Mechanical properties and equilibrium swelling degree of the hydrogels can be controlled by varying the ratio of HA pyridyl disulfide and macro-cross-linker PEG-dithiol. Degradation of the hydrogels was achieved both enzymatically and chemically by disulfide reduction with distinctly different kinetics and profiles. In the presence of hyaluronidase, hydrogel mass loss over time was linear and the degradation was faster at higher enzyme concentrations, suggesting surface-limited degradation.

The viscosity of these polymers could be controlled by using its pH properties. The low viscosity region during low pH environment helps with deployment of the augmentation gel because the gel has to be delivered through a small diameter tubing. Polymers that are pH sensitive are also called polyelectrolytes. The swelling properties of polyelectrolyte networks, which can be described in terms of the swelling rate and maximum solution uptake at equilibrium, depend on the physicochemical properties of the polymers and on the composition of the surrounding medium. Polyelectrolyte gels change their conformation with the degree of dissociation which is the function of quantities such as pH value, polarity of the solvent, ionic strength and temperature of the external environment solution.

Example C

Another preferred embodiment is filling a silicone shell with cross-linked hyaluronic acid material. This method required a high sheer mixer. The HA is cross linked using available cross-linkers such as divinyl sulfone, 1,4-butane diol diglycidyl ether in the presence of 0.1M sodium hydroxide. When the crosslinking reaction has completed, the HA gel is washed repeatedly until the residual cross-linker was no longer detectable in the HA gel, At this point, the cross-linked gel is blended with 10% water in shear mode to create uniform and small particles. The blended cross-linked material reformulated with un-cross-linked materials HA for injectability and longevity.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast, butt or body implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Figure 7B:
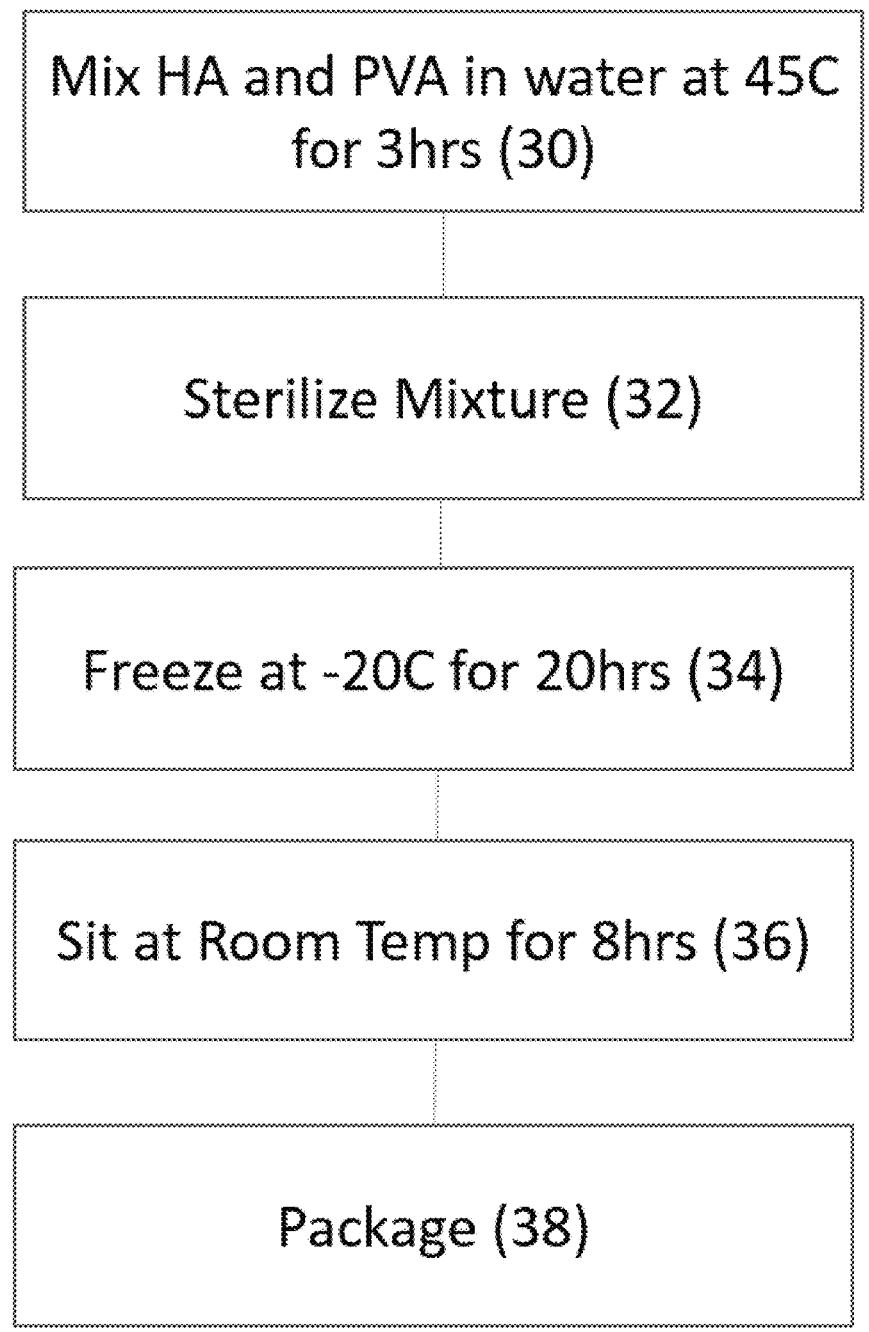

FIGS. 7A-7E show exemplary hydrogel fabrication processes that can produce large volume of gels for minimally invasive body augmentation. In FIG. 7A, hyaluronic acid (HA) and poly vinyl alcohol (PVA) are mixed with distilled water as a batch at 45° C. for about 3 hours (10). The mixture can have from about 95% to 80% PVA. PVA is a highly hydrophilic polymer with a chemical formula of $(C_2H_4O)_n$ and the structural formula is $(—CH_2CH(OH)—)_n$. HA is an anionic, nonsulfated glycosaminoglycan distributed widely throughout connective, epithelial, and neural tissues. The mixture of HA-PVA is frozen at −20° C. for about 20 hours (12) and the batch is allowed to warm to room temperature for about 8 hours (14). In general, slower thawing leads to less leachable polymer. A more efficient gelation process can be achieved with decreasing thaw rates. The shear modulus of the hydrogel increases approximately linearly with decreasing log of the thawing rate. The batch is then sterilized and packaged (16). The sterilization can be done using an autoclave, which is a pressure chamber used to sterilize the HA-PVA gel by subjecting them to high pressure saturated steam at 121° C. (249° F.) for around two hours depending on the size of the load and the contents.

When PVA in aqueous solution (or in aqueous/DMSO mixtures) is heated to dissolution and then frozen and thawed repeatedly, it forms a highly elastic gel. The solgel transition forms a physically (not chemically) crosslinked polymer. Thus, the crosslinking that is achieved is thermoreversible. There is a dependence of the cryogel characteristics on the molecular weight of the uncrosslinked polymer, the concentration of the aqueous solution, temperature and time of freezing, the heating/cooling rates and the number of freeze-thaw cycles. Thus, there is a rich parameter space from which control of the mechanical properties of the PVA cryogels may be exercised. PVA cryogels exhibit very low toxicity (at least partially due to their low surface energy), contain few impurities and their water content can be made commensurate to tissue at 80 to 90 wt % and are thus generally considered to be fairly biocompatible.

In FIG. 7B, a similar process is done, but the sterilization is done prior to freezing. First, the HA and PVA are mixed with distilled water as a batch at 45° C. for about 3 hours (30) and sterilized in the autoclave oven (32). The result is frozen at −20° C. for about 20 hours (34) and the batch is allowed to warm to room temperature for about 8 hours (36). The batch is then packaged (38).

In FIG. 7C, the mixture of HA and PVA is done (50), and the mixture is sterilized (52). One or more cycles of freeze/thaw of the mixture is done (54), and the final thaw to room temperature is done and the product is then packaged as a sterile solution (56).

The swelling of PVA-HA gels at any time point decreases with increasing number of freeze-thaw cycles, indicating a densification of the PVA gel, most likely due to a higher crosslink density. In the long term, following gelation and under static conditions, the ultimate swelling ratio decreases while the modulus increases with time. In freeze-thaw processing, temperature is used to force a phase separation of the PVA solution, thus enhancing the gelation mechanism in the PVA (it should be noted that even at room temperature a solution of PVA begins to gel weakly over time). However, as HA is not affected by the number of freeze-thaw cycles, the presence of HA provides stability of the resulting gel.

FIG. 7D shows another process to form body augmentation hydrogel where the sterilization is done prior to freezing. First, the HA and PVA are mixed with distilled water as a batch at 45° C. for about 3 hours (70) and sterilized (72). One or more freeze/thaw cycles are done, where each time the mixture is frozen at −20° C. for about 20 hours and the batch is allowed to warm to room temperature for about 8 hours (74). The batch is then packaged (78).

Freeze/thaw cycling of PVA polymer in solution results in the formation of physical cross-linking (i.e. weak bonding through a nonpermanent "association" of the polymer chains). PVA hydrogels formed in this manner are thermoreversible and are termed "cryogels". In general, cryogels are solid elastomers containing over 80% water which are produced when solutions of higher molecular weight poly (vinyl alcohol) (PVA) of high degree of hydrolysis are subjected to one or more freeze-thaw cycles. Such cryogels are tough, slippery, elastomeric, resilient, insoluble in water below 50 degrees Celsius, and nontoxic. Freeze-thaw cycling of solutions of PVA polymer results in the formation of physical associations (i.e. weak bonding through an "association" of the polymer chains). PVA hydrogels formed in this manner are termed "cryogels" and are described, for example, in U.S. Pat. Nos. 6,231,605 and 6,268,405, 7,235,592, the entire contents of which are incorporated herein by reference. All references, patents, patent applications or other documents cited are hereby incorporated by reference herein in their entirety.

Importantly, the techniques utilized to create PVA cryogels do not require the introduction of chemical crosslinking agents or radiation. Cryogels are therefore easily produced with low impact on incorporated bioactive molecules. However, incorporated molecules are limited to those that can tolerate the freeze-thaw cycles required to make the gel. Thus the resulting material can contain bioactive components that will function separately following implantation. PVA cryogels are also highly biocompatible (as are PVA "thetagels," discussed below). They exhibit very low toxicity (at least partially due to their low surface energy), contain few impurities and their water content can be made commensurate to that of tissue at 80 to 90 wt %. In the preferred embodiment, HA is provided to cross-link with the PVA to provide additional biocompatibility and tissue like feeling to patients. HA is unique among glycosaminoglycans in that it is nonsulfated, forms in the plasma membrane instead of the Golgi, and can be very large, with its molecular weight often reaching the millions. HA is a polymer of disaccharides, themselves composed of D-glucuronic acid and D-N-acetylglucosamine, linked via alternating β-1,4 and β-1,3 glycosidic bonds. Hyaluronic acid can be 25,000 disaccharide repeats in length. Polymers of hyaluronic acid can range in size from 5,000 to 20,000,000 Da in vivo. The average molecular weight in human synovial fluid is 3-4 million Da Cross-linked versions of HA have been approved by the FDA for use as a dermal filler.

While the autoclave oven can be used to sterilize the composition, certain embodiments use e-beam for sterilization. Electron beam processing or electron irradiation is a process which involves using electrons, usually of high energy, to treat an object for a variety of purposes. This may take place under elevated temperatures and nitrogen atmosphere. The preferred embodiment uses e-beam for electron irradiation to provide sterilization and to cross-link polymers. Instead of ebeam, X-ray or suitable radiation types can be used to cross-link the PVA.

In FIG. 7E, the HA and PVA is mixed in water (80) and then ebeam is used to sterilize and crosslinking the HA-PVA mixture (82). Instead of ebeam, X-ray or suitable radiation types can be used to cross-link the PVA. Next, the system can optionally perform zero or more freeze/thaw cycles (84) before the mixture is packaged for use (86).

Poly(vinyl alcohol) useful is typically obtained as a dry powder or crystal, and can vary based upon several factors, including molecular weight, degree of polymerization, and degree of saponification (or hydrolysis). The molecular weight of the poly(vinyl alcohol) can vary, and can be chosen depending upon the particular application envisioned for the hydrogel. Generally, increasing the molecular weight of the poly(vinyl alcohol) increases the tensile strength and tensile stiffness, and thereby improves the properties of constructs such as vascular grafts, wherein increased strength is desirable. In other applications, such as a nerve bridge, lower molecular weight poly(vinyl alcohol) can be employed because lower tensile strength and lower tensile stiffness are desirable. Poly(vinyl alcohol) having an average molecular weight of from about 11,000 to 500,000 is preferred for practicing the invention. Poly(vinyl alcohol) having an average molecular weight of from about 85,000 to 186,000 is even more preferred for practicing the invention, especially when producing vascular grafts, and poly(vinyl alcohol) having an average molecular weight of from about 124,000 to 186,000 is especially preferred.

The water that is mixed with the HA-PVA preferably undergoes deionization, reverse osmosis and ultra-filtered to minimize the potential for any contamination of the HA-PVA. The concentration of the poly(vinyl alcohol) contributes to the stiffness of the hydrogel and can thus be chosen depending upon the stiffness of the material one desires to obtain. A more preferable mixture is obtained by mixing from about 10 to about 30 parts HA-PVA with from about 70 to about 90 parts by weight water, and an especially preferred mixture is obtained by mixing about 25 parts HA-PVA with about 75 parts by weight water. Isotonic saline (0.9% weight to volume in water) or an isotonic buffered saline may be substituted for water to prevent osmotic imbalances between the material and surrounding tissues if the hydrogel is to be used as a soft tissue replacement.

After the poly(vinyl alcohol) and water are mixed, it is often necessary to process the mixture to ensure that the poly(vinyl alcohol) is adequately solubilized. Suitable solubilization processes are generally known in the art and include, for example, heating the mixture, altering the pH of the mixture, adding a solvent to the mixture, subjecting the mixture to external pressure, or a combination of these processes. A method is to heat the mixture at a temperature of about 95° C.-120° C., for a period of time not less than 15 minutes and the one way of doing this, is an autoclave which also sterilizes the mixture before further processing.

After the mixture has been prepared, air bubbles that may have become entrapped in the mixture are removed. The solution can be allowed to sit for a period of time at an elevated temperature, to allow the air bubbles to rise out of solution. The mixture can also be placed in a sterile vacuum chamber for a short time to bring the bubbles out of solution. The mixture can also be centrifuged at an elevated temperature to bring the bubbles out of solution.

In yet another embodiment, a process produces the HA-PVA hydrogel in a two stage process. In the first stage a mixture of HA-PVA and water is placed in a mold, and repeatedly frozen and thawed, in cycles, until a suitable HA-PVA hydrogel is obtained. In a second stage, the HA-PVA hydrogel is removed from the mold, placed in water, and undergoes at least one other freeze-thaw cycle until desirable mechanical properties are achieved. In the first stage, a series of sequential steps is employed comprising: (i) mixing water with HA-PVA to obtain HA-PVA/water mixture; (ii) freezing the mixture; (iii) thawing the mixture; and (iv) repeating the freeze and thaw steps, as necessary, until an HA-PVA hydrogel having the desired physical properties is obtained. If necessary, the second stage may then be employed.

Figure 8A:
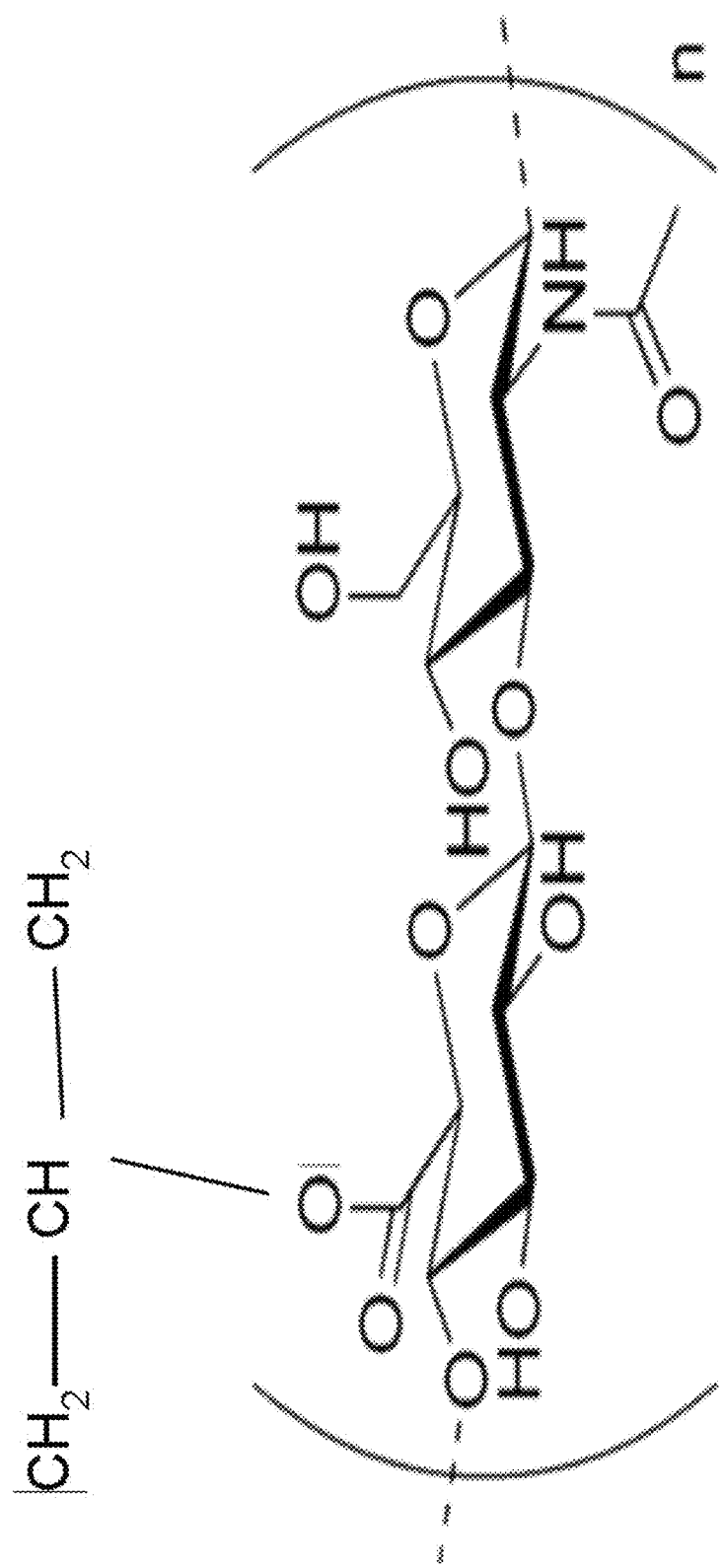
Figure 8B:
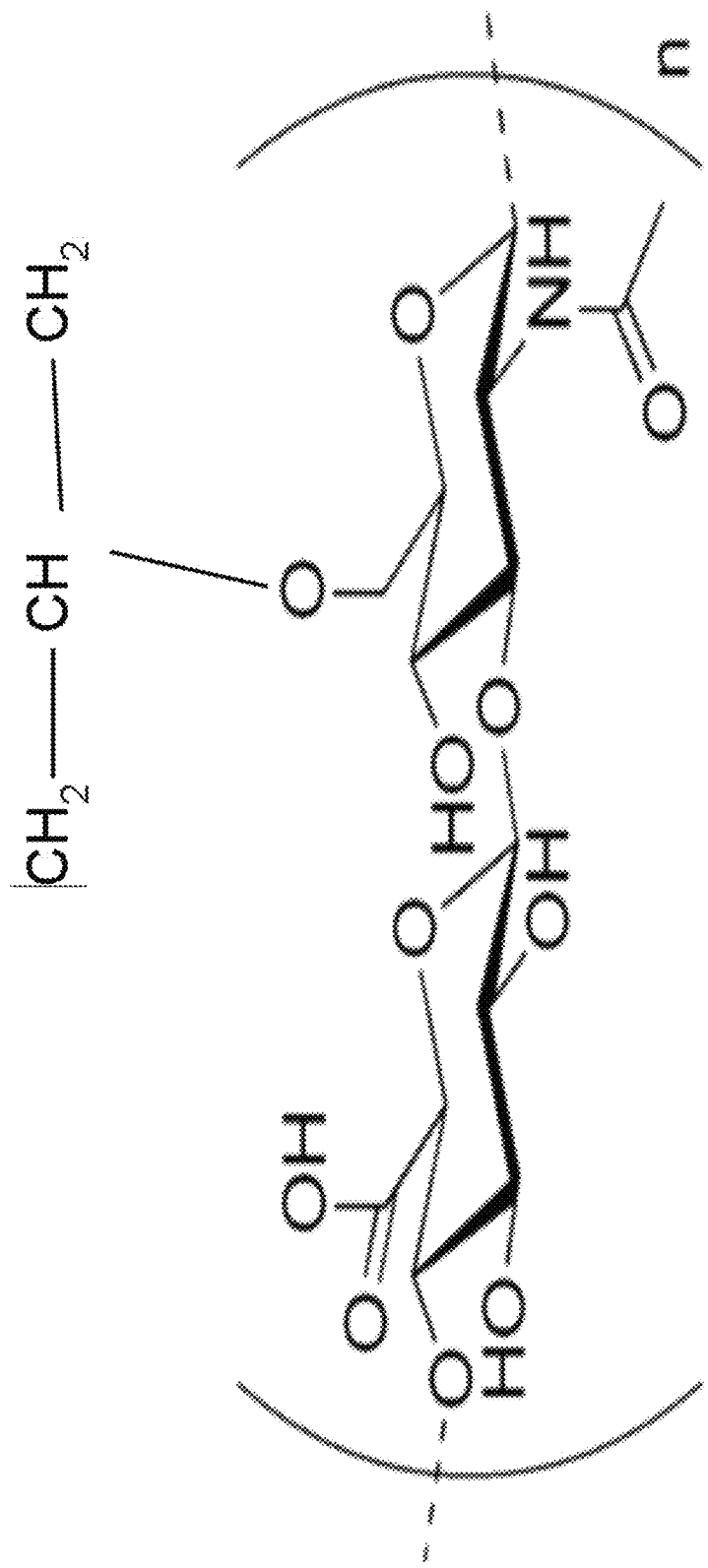
FIG. 8B shows ether bonding.

FIG. 8A shows exemplary HA-PVA bonding configurations with ester bonding, while FIG. 8B shows exemplary ether bonding configurations for HA-PVA. Crosslinks in HA-PVA gels may be either covalent (chemical) crosslinks or physical associations (physical). Covalent crosslinks are formed typically through chemical modification, or through irradiation. Physical associations may be formed via freeze-thaw cycling, dehydration or through controlled manipulation of the solubility of the vinyl polymer in a solvent (to produce a "thetagel"), disclosed in U.S. published patent application Ser. No. US20040092653 or by a combination of such methods. In general, the formation of a thetagel includes a step of mixing the vinyl polymer solution with a gellant, wherein the resulting mixture has a higher Flory interaction parameter than the vinyl polymer solution. In the present invention, both covalent and physical associations can be employed, in that a physically cross-linked precursor gel will be covalently crosslinked by irradiation. The use of irradiation to form covalent crosslinks has several advantages over chemical crosslinking. Chemical crosslinking is often performed by the addition of a reactive metallic salt or aldehyde and subjecting the system to thermal radiation. For example, crosslinking may be performed by adding (di-)isocyanates, urea-/phenolic-melamine-resins, epoxies, or (poly-)aldehydes. However, the use of such reagents for chemical crosslinking can leave residues that decrease the biocompatibility of the PVA hydrogel.

Crosslink formation by irradiation of polymers in solution is a suitable method for the generation of hydrogels for biomedical use. Crosslinking via an ionization source provides adequate control of the reaction, a lower number of unwanted processes (e.g. homografting of monomer to the side of a polymer chain) and generates an end product suitable for use with little additional processing or purification. The irradiation and sterilization steps can often be combined.

The graph of FIG. 9 shows the temperature effect use on the sterilized gel at 25 C and 37 C. In general, high temperature reduces the elasticity and viscosity of the gel. FIG. 8's graph also illustrates differences between the sterilized PVA-HA gel and Juvederm gel at 25 C—the sterilized gel has higher viscosity and elasticity than the Juvederm gel at the same temperature 25 C. The unsterilized gel acts as a fluid.

Figure 10:
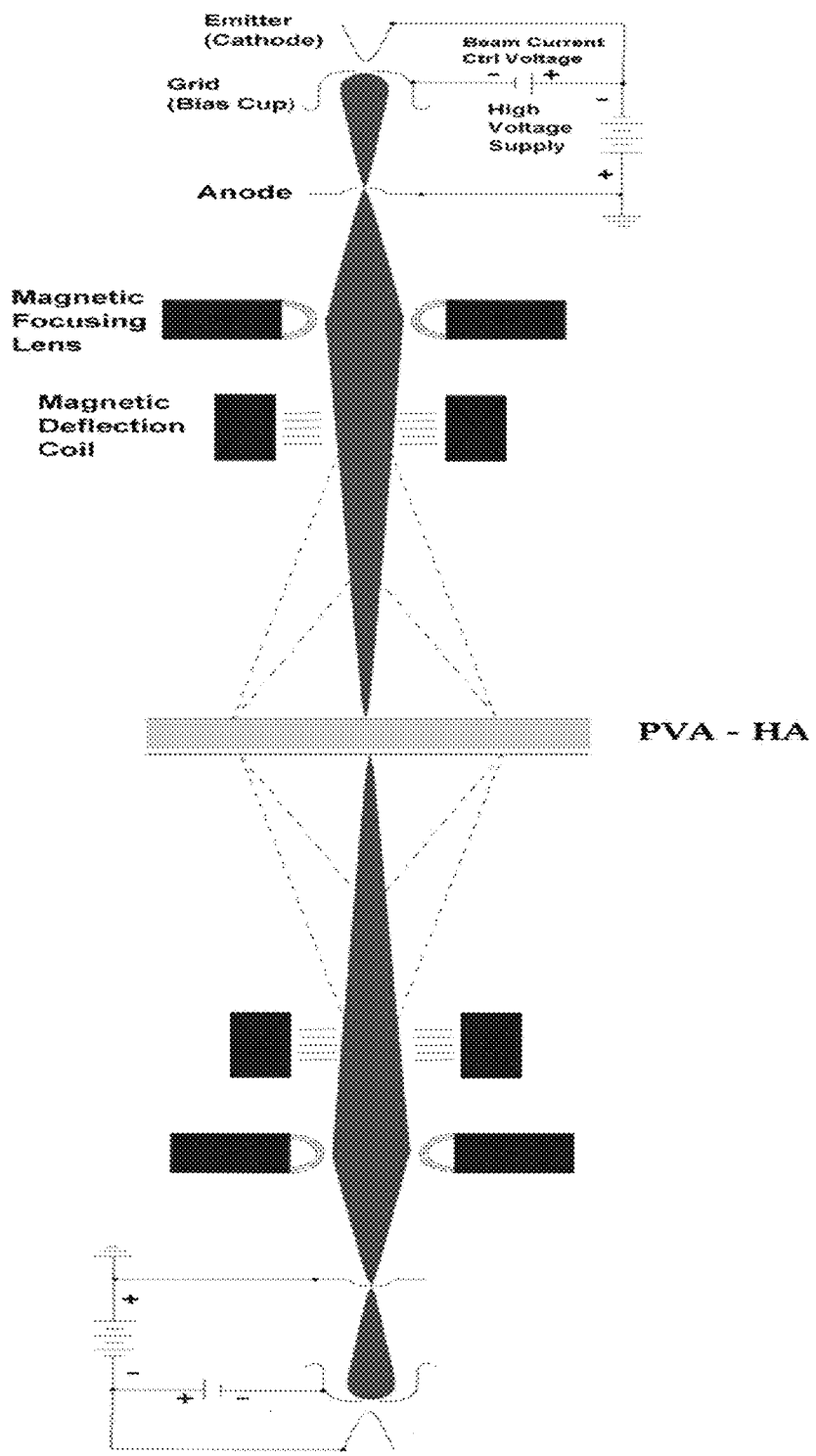
FIG. 10 shows an exemplary ebeam cross-linking system.

FIG. 10 shows a dual electron beam processing device are illustrated in the figure. In each portion, an electron gun (consisting of a cathode, grid, and anode) is used to generate and accelerate the primary beam. A magnetic optical (focusing and deflection) system is used for controlling the way in which the electron beam impinges on the HA-PVA mixture being processed. In operation, the gun cathode is the source of thermally-emitted electrons that are both accelerated and shaped into a collimated beam by the electrostatic field geometry established by the gun electrode (grid and anode) configuration used. The electron beam then emerges from the gun assembly through an exit hole in the ground-plane anode with an energy equal to the value of the negative high voltage (gun operating voltage) being applied to the cathode. This use of a direct high voltage to produce a high energy electron beam allows the conversion of input ac power to beam power at greater than 95% efficiency, making electron beam material processing a highly energy-efficient technique. After exiting the gun, the beam passes through an electromagnetic lens and deflection coil system. The lens is used for producing either a focused or defocused beam spot on the workpiece, while the deflection coil is used to either position the beam spot on a stationary location or provide some form of oscillatory motion. Dual Electron Beam Processing for high volume production doubles processing rates, ensures 100% system uptime, and virtually eliminates processing delays. The dual design minimizes stress via Gaussian electron waves for continuous and normalized distribution of energy. In one HA-PVA ebeam embodiment, an electron beam may be used on the material to induce effects such as chain scission (which makes the polymer chain shorter) and cross linking. The result is a change in the properties of the polymer which is intended to extend the range of applications for the material. The effects of irradiation may also include changes in crystallinity as well as microstructure. Usually, the irradiation process degrades the polymer. The irradiated polymers may be characterized using FTIR to confirm cross-linking presence.

The HA-PVA hydrogel can be irradiated while masked by a centrally placed aluminum disk to produce a step change in radiation dose between masked and exposed regions of the hydrogel. Shielding can be utilized to crosslink PVA disks with a stepped difference in radiation crosslinks. In one embodiment the shielding is made from a material with a uniform density and thickness. In other embodiments, different locations of the shield can have different thickness or different density and shaped to determine the area and degree of reduced radiation effectiveness. The material will block radiation (e-beam or gamma) in proportion to the thickness of the shielding piece. Following radiation crosslinking, the gel can be held at high temperature to melt-out the physical associations producing a PVA hydrogel having a gradient of crosslinks.

In one embodiment, a method of making a cross-linked vinyl polymer hydrogel includes providing a physically crosslinked HA-PVA hydrogel having a crystalline phase using freeze/thaw; exposing the physically crosslinked vinyl polymer hydrogel to an amount of ionizing radiation providing a radiation dose in the range of about 1-1,000 kGy effective to form covalent crosslinks; and removing the physical associations by exposing the irradiated vinyl polymer hydrogel to a temperature above the melting point of the physically associated crystalline phase to produce a cross-linked HA-PVA hydrogel. In preferred embodiments, the step of providing a physically associated vinyl polymer hydrogel having a crystalline phase includes the steps of providing a vinyl polymer solution comprising a vinyl polymer dissolved in a solvent; heating the vinyl polymer solution to a temperature elevated above the melting point of the physical associations of the vinyl polymer; inducing gelation of the vinyl polymer solution; and controlling the gelation rate to form physical associations in the vinyl polymer hydrogel. In preferred embodiments, the vinyl polymer is selected from the group consisting of poly(vinyl alcohol), poly(vinyl acetate), poly(vinyl butyral), poly(vinyl pyrrolidone) and a mixture thereof. Preferably, the vinyl polymer is poly(vinyl alcohol).

In preferred embodiments, the solvent of the vinyl polymer solution is selected from the group consisting of deionized water, methanol, ethanol, dimethyl sulfoxide and a mixture thereof. In preferred embodiments, the irradiated vinyl polymer hydrogel is immersed in a solvent is selected from the group consisting of deionized water, methanol, ethanol and a mixture thereof while is exposed to a temperature above the melting point.

In another aspect, systems and methods are disclosed for cosmetic augmentation of soft tissue using cross-linked HA-PVA that had been optimized for
1. ease of product delivery,
2. local tissue compliant,
3. greater cohesiveness to control migration of the implant material and
4. bio-degradation profile.

The use of a particularly cross linked HA, and cross linked by forming regions of interpenetrating network (IPN) of cross linked HA by further crosslinking them. The IPN configuration gives this cross linked HA those utilities unique for this cosmetic augmentation application. The IPN core is more resistance to biodegradation in a human body than the single cross-linked material normalized for the same cross linking level. Furthermore, varying physical properties that continuously changes radiating out from the core makes the polymer tough and at the same time compliant with the local tissue for better tissue/device biocompatibility and feels more natural to the touch.

The above HA cross linking method optimized for cosmetic augmentation in certain cases may need to control delivered pharmaceutical substances to modulate local tissue response to the polymer. The pharmaceutical component makes up the multi-phase mixture with the other phase being the cross linked HA polymer.

Implementations of the above aspects may include one or more of the following. The system is biocompatible and performs controlled drug releases at strategic timing to coincide with key physiological events. For example, a fast drug release profile and no delay would be well suited for the controlled release of an anesthetic such as lidocane to relieve acute pain experienced by the patient associated with the surgical procedure. The system is also capable of a medium release profile and a medium delay of a corticosteroid or steroid such as dexamethasone or triamcinolone to co-inside with a physiological inflammatory foreign body reaction. The system can also be customized to have a medium to slow release profile and a longer delay before starting the release of an antiproliferative drug such as paclitaxel, serolimas or 5-flourouracil to stop uncontrolled healing and excessive remodeling causing unsightly scar formation or capsular formation.

Another aspect of the present invention includes methods for optimizing biodegradation profiles and control migration of the implant material through the manipulation of various types molecular weight. The system optimizes biodegradation profiles and controls migration of the implant material. The system can be formulated around various types of molecular weights such as $M_n$, $M_w$ and $M_z$, and their polydispersity index (PDI) to optimize the biodegradation profiles to be from hypervolumic to isovolumic to hypovolumic.

The degradation reaction by oxygen derived free radical of HA was the results of studies using the HA present in synovial fluids. It showed that the HA was readily degraded by super oxide free radicals. This reaction is most favorable in the case of secondary free radicals. Neutrophils (polymorphonuclear leukocytes) produced the type of oxygen derived free radicals that allowed it phagocytotically consumed HA molecules. These WBC's are by far the exclusive destroyers of HA by oxygen-derived free radical mechanism. Thus, an aspect of this invention is to quench the effect of the free radical before it degrades the HA using free radical scavengers such as antioxidant vitamins.

Antioxidants are intimately involved in the prevention of cellular damage—the common pathway for cancer, aging, and a variety of diseases. Antioxidants are molecules which can safely interact with free radicals and terminate the chain reaction before vital molecules are damaged. The system can incorporate antioxidant enzymes to protect the longevity of HA. These enzymes can reduce the radicals and defend against ROS. They are: alpha-1-microglobulin, superoxide dismutases, catalases, lactoperoxidases, glutathione peroxidases and peroxiredoxins.

The system can apply different dose ranges to different areas of the same product at the same time so that the PVA-HA can have an inner core that is highly cross-linked while keeping the outer core with reduced HA crosslinking to provide enhanced bio-compatibility.

In various embodiments, cross-linked vinyl polymer hydrogels are produced by making a physically associated vinyl polymer hydrogel having a crystalline phase, exposing the physically associated vinyl polymer hydrogel to an amount of ionizing radiation providing a radiation dose that is effective to form covalent crosslinks, and removing physical associations by exposing the irradiated vinyl polymer hydrogel to a temperature above the melting point of the physically associated crystalline phase to produce a covalently cross-linked vinyl polymer. Typically the radiation dose is in the range of about 1-2,000 kGy. The physical properties of the produced hydrogel can be adjusted by varying controlled parameters such as the proportion of physical associations, the concentration of polymer and the amount of radiation applied. Such covalently crosslinked vinyl polymer hydrogels can be made translucent, preferably transparent, or opaque depending on the processing conditions. The stability of the physical properties of the produced vinyl polymer hydrogel can be enhanced by controlling the amount of covalent crosslinks. Preferably the fraction of physical associations removed ranges from about one tenth to substantially all of the physical associations. In other preferred embodiments, about 1-90% of the physical associations are removed.

In accordance with a preferred embodiment, the method of manufacturing a crosslinked vinyl polymer hydrogel includes the steps of providing the HA-PVA solution comprising a vinyl-HA polymer dissolved in a solvent; heating the vinyl-HA polymer solution to a temperature elevated above the melting point of the physical associations of the vinyl polymer, inducing gelation of the vinyl polymer solution; controlling the gelation rate to form crystalline physical associations in the vinyl polymer hydrogel, exposing the physically associated vinyl polymer hydrogel to a dose of ionizing radiation of about 1-1,000 kGy effective to produce covalent crosslinks and melting the vinyl polymer hydrogel in a solvent to remove substantially all or a fraction of the physical associations. In some preferred embodiments, the produced covalently crosslinked vinyl polymer hydrogel substantially lacks physical associations.

The desired physical property typically includes at least one of light transmission, gravimetric swell ratio, shear modulus, load modulus, loss modulus, storage modulus, dynamic modulus, compressive modulus, crosslinking and pore size.

In preferred embodiments, HA is mixed with the vinyl polymer, which is selected from the group consisting of poly(vinyl alcohol), poly(vinyl acetate), poly(vinyl butyral), poly(vinyl pyrrolidone) and a mixture thereof. Preferably the vinyl polymer is highly hydrolyzed poly(vinyl alcohol) of about 50 kg/mol to about 300 kg/mol molecular weight. In preferred embodiments, the vinyl polymer is highly hydrolyzed poly(vinyl alcohol) of about 100 kg/mol molecular weight. Typically the vinyl polymer solution is about 0.5-50 weight percent solution of poly(vinyl alcohol) based on the weight of the solution. In certain preferred embodiments, the vinyl polymer solution is about 1-15 weight percent. In other preferred embodiments, the vinyl polymer solution about 10-20 weight percent polyvinyl alcohol. The vinyl polymer, preferably poly(vinyl alcohol), can be isotactic, syndiotactic or atactic.

The solvent of the vinyl polymer solution is selected from the group consisting of deionized water (DI), methanol, ethanol, dimethyl sulfoxide and a mixture thereof. The solvent used in melting the vinyl polymer hydrogel to remove the physical associations is selected from the group consisting of deionized water, methanol, ethanol, dimethyl sulfoxide and a mixture thereof. In preferred embodiments, the same solvent is used for the vinyl polymer solution and for melting the vinyl polymer hydrogel to remove the physical associations.

In preferred embodiments, the ionizing radiation is X-ray, gamma radiation or beta particles (electron beam). In preferred embodiments, the total radiation dose is suitably 1-1,000 kGy, preferably 50-1,000 kGy, more preferably 10-200 kGy. The radiation dose rate is suitably about 0.1-25 kGy/min, preferably about 1-10 kGy/min. In preferred embodiments, the irradiation dose used is within 20% of the optimum irradiation dose, preferably within 10%, more preferably within 7% of the optimum irradiation dose. The optimum irradiation dose is specific to each polymer.

In preferred embodiments, the suitable polymer concentration of the hydrogel product to be irradiated can be optimized within the polymer concentration range flanking the maximum of a plot of intermolecular crosslinking yield v. polymer concentration or the minimum of a plot of irradiation dose v. polymer concentration, i.e. the point at which the slope of the plot is zero. Suitably, the polymer concentration falls in a range in which the intermolecular crosslinking yield or the irradiation dose is within 20% of the maximum or minimum value, respectively, preferably within 10%, more preferably within 7% of the value. Where the hydrogel comprises poly(vinyl alcohol), the hydrogel is suitably about 2 to about 35 weight percent poly(vinyl alcohol), preferably about 3.5 to about 30 weight percent poly(vinyl alcohol), more preferably about 5 to about 25 weight percent poly(vinyl alcohol), based on the weight of the composition.

After irradiation, the physical associations are removed by raising the temperature of the hydrogel above the melting point of the thermo-reversible physical associations. The required temperature depends on the melting point of the cross-links and is suitably about 0-100 degrees Celsius, preferably about 40-80 degrees Celsius. Preferably the irradiated gels are heated to high temperatures while they are immersed in solvent to allow dissolution and elution of the PVA chains "melted out" of the physical associations. The duration of the exposure to the elevated temperature can be adjusted to melt out all of the physical associations, or just a fraction of the physical associations.

The crosslinked vinyl polymer hydrogels of the present invention have an advantageous inherent material stability that is exhibited when the crosslinking is covalent chemical rather than physical. Forming covalent crosslinks by radiation rather than by chemical reagents avoids the potential problem of residual contaminants. For medical materials and articles of manufacture, both the irradiation and the sterilization steps can be performed simultaneously, simplifying manufacturing and reducing costs. The ability to control pore size by varying the degree of precursor gel physical crosslinking will be an advantage over other means of forming covalent vinyl polymer hydrogels.

Figure 11:
FIG. 11 shows an exemplary hydrogel fabrication process that can produce large volume of gels with anti-inflammatory drugs or agents.

The method can include timing the switch to match the typical time for development of tissue encapsulation (timing approach) or to have the encapsulation event itself trigger the switch (event triggered approach). FIG. 11 shows an exemplary hydrogel fabrication process that can produce large volume of gels with anti-inflammatory drugs or agents. In FIG. 11, the HA and PVA, along with an anti-inflammatory drug, are mixed with distilled water as a batch at 45° C. for about 3 hours (130) and sterilized in the autoclave oven (132). The result is frozen at −20° C. for about 20 hours (134) and the batch is allowed to warm to room temperature for about 8 hours (136). The batch is then packaged (138).

In another form of the present invention, a biodegradable layer can be formed on the HA-PVA material to act as a switch to turn on the release of an extracellular matrix (ECM) suppressing therapeutic agent (i.e. fluoroquinolone, glucosamine, diethylcarbamazine, etc.). Exemplary fluoroquinolones include ciprofloxacin, levofloxacin, and moxifloxacin. The drug can be ciprofloxacin which is an antibiotic in a group of drugs called fluoroquinolones. In one embodiment, the Cipro can be sprayed or otherwise atomized onto the implant surface. In another embodiment, the implant can be submersed in a solution with Cipro and a binder can be provided to bind the Cipro to the implant. Ciprofloxacin fights bacteria in the body. Ciprofloxacin is used to treat different types of bacterial infections. It is also used to treat people who have been exposed to anthrax. Other medications can be used, for example, leukotriene receptor antagonists, such as zafirlukast (Accolate®), montelukast (Singulair®), and pranlukast administered orally can moderate the capsular contracture. Other medications include antibiotics surrounding the implant Finally, textured implants have yielded a reduction in capsule formation.

Under the timing approach, a biodegradable layer can be coated on the therapeutic agent matrix that would degrade enough to allow therapeutic agent elution around 20 to 40 days, the typical time of tissue encapsulation of an implant. The layer could be configured to degrade in tissue and/or in blood. For the switch to be effective, it must effectively block ECM suppressing therapeutic agents from eluting for the duration of Encapsulation Development Time and then quickly turn on to fully elute a therapeutic agent to block proteoglycans (i.e. versican, decorin, biglycan), hyaluronan, inter-a-trypsin and/or collagen (types I and III) from being further synthesized and deposited. In this way significant ECM-related restenosis is prevented since proteoglycans and collagen are the dominant components of ECM. The ECM is responsible for the bulk of restenosis in the long term.

Since the typical ECM suppressing therapeutic agent (i.e. fluoroquinolone) is hydrophilic, a good solid barrier layer should be made of a hydrophobic or slightly hydrophobic substance to control the elution time and degradation time to better match the Encapsulation Development Time. This outer barrier layer of a more hydrophobic substance can be selected from polylactic acid (PLA), polyglycolic acid (PGA), a copolymer of PLA and PGA (PLGA), polycaprolactone (PCL), other biodegradable polyesters, polyamino acids, or other hydrophobic, biodegradable polymers.

Preferably, under the barrier layer and immediately adjacent to the therapeutic agent matrix layer another layer is provided that is instead slightly hydrophilic or closer in polarity to the therapeutic agent itself than the outer barrier layer. This middle layer is the key to the rapid, burst characteristic of therapeutic agent elution while the outer barrier layer is the key to the delayed onset characteristic of therapeutic agent elution. As an alternative or as a complement to providing a separate layer beneath the barrier layer that is opposite in polarity to the barrier layer and closer in polarity to the therapeutic agent, the material used to form the therapeutic agent soluble material can be provided in pockets distributed throughout the barrier layer. By interspersing the barrier matrix with pockets of a hydrophilic substance (i.e. dextran, heparin) a switch effect for accelerated barrier layer degradation and therapeutic agent elution can be better achieved. Upon a threshold level of water penetration into the barrier matrix containing the pockets, the pockets increase in pressure to the point where they burst to destroy the barrier structure. The pockets act as isolated reservoirs or oases for hydrophilic physiologic and other fluids that the barrier layer's base material does not readily accept. Although the biodegradation of the barrier layer may be directed by other means such as the emergence of a restenotic environment in which the barrier layer dissolves, the incorporation of pockets allows additional options for fine-tuning the timing of barrier degradation by also making it indirectly susceptible to hydrophilic fluids and environments.

If the therapeutic agent happens to be hydrophobic rather than hydrophilic the polarities (hydrophobicity and hydrophilicity) of the respective matrices, layers, and/or pockets should be reversed. The bottom line is that the outermost barrier layer is to be opposite in polarity to the therapeutic agent and the inner layer(s) or pocket(s) that are closer to the therapeutic agent are closer in polarity to the therapeutic agent. However, preferably the therapeutic agent itself is contained in a matrix that is opposite in polarity for stabilization. The design is sandwich-like in configuration with the outer barrier and the therapeutic agent matrix analogized to pieces of bread between the unique opposite polarity inner layer or pockets analogized to the meat. The inner opposite polarity layer is the trigger to burst elution because the therapeutic agent easily dissolves within it suddenly and completely.

Under the event triggered approach, there are several ways to trigger the switch to allow therapeutic agent elution to occur upon tissue encapsulation of the implant:

1. First, the coating covering the therapeutic agent matrix is designed to immediately break down to allow therapeutic agent elution upon tissue encapsulation. This can be achieved by coating the therapeutic agent matrix with a slightly to hydrophobic, biodegradable outer barrier layer that breaks down quickly upon the presence of a slightly to very hydrophobic environment such as provided by restenotic material. A thin layer of wax or a fatty substance exemplify the type of coating to be used. Specific examples of these include lipoprotein, collagen, polyamino acids, PLA, PLGA, and polycaprolactone, 2. Second, the ECM suppressing therapeutic agent can be bound to a molecule that inactivates the therapeutic agent until ECM factors (i.e. collagen, proteoglycans) are present.

3. Third, the switch can be turned on by other factors accompanying tissue encapsulation or extracellular matrix thickening including: hormones, enzymes, and/or peptides, etc.

4. Fourth, pressure can be used to induce release of the therapeutic agent, i.e. by housing the therapeutic agent within a semi-permeable membrane that bursts or by including pressure-building pockets within a barrier layer.

5. Fifth, pH changes can be used to induce release of the therapeutic agent if the material retaining (i.e. coating or serving as a matrix for) the therapeutic agent is sensitive to acids or bases and degrades (in tissue or in blood) upon being subjected to acidic or basic environments. In one embodiment, the therapeutic agent is coated with a slightly hydrophobic, acid-sensitive layer of PLGA. Tissue encapsulation of the implant can trap the PLGA and the acids produced from PLGA degradation. Subsequently, the concentration of acids is dramatically increased which leads to rapid degradation of the PLGA itself.

This event triggered approach offers a high degree of control of therapeutic agent elution and/or activation. The onset of therapeutic agent elution and/or the catalyst for therapeutic agent activation is particularized to occur independently and exclusively on the implant localities encapsulated by tissue while the elution is restrained and/or the therapeutic agent remains dormant and inactive on the implant localities that are still bare and unencapsulated. Encapsulation rates vary between procedures, individuals, and implant localities. Therefore, event-triggered therapeutic agent control provides an individualized approach for enhanced accuracy, safety and effectiveness.

It is preferred that the dosage of the anti-restenosis therapeutic agent is higher at the ends of the implant to compensate more aggressive restenosis at the ends of the implant.

The AMF/ANF/AG material may take the form of a coating, a matrix, or an implant body so long as its structure and orientation are such that it can both facilitate endothelization and also delay the onset of therapeutic agent release, if therapeutic agents are used. Preferably, the AMF/ANF/AG material lasts for 15-30 days before it is fully degraded to expose the therapeutic agent underneath. However, it may work by fully degrading anywhere between 5-60 days. The AMF/ANF/AG material is preferably made of PGA or a copolymer of PGA-PLA. These are proven compounds used on DES as well as biodegradable sutures and are well documented for their compatibility with blood. PGA and PGA-PLA are especially well suited to degrade within 15-30 days. The delay time before onset of release of the ECM suppressing therapeutic agent (i.e. fluoroquinolone, glucosamine, diethylcarbamazine, etc.) is equal to the time it takes the AMF/ANF/AG material to fully degrade. This delay time is controlled by the exact chemical compounds used to create the coating and also the coating thickness. For example, since 50% PLA:50% PGA degrades more quickly than a 75% PLA:25% PGA mix, to obtain the same therapeutic agent release onset delay a thicker layer of 50% PLA:50% PGA would be used than if a 75% PLA:25% PGA mix were used. The AMF/ANF/AG material is preferably between 0.1 micron and 20 microns thick.

Alternatively, instead of PGA and/or PLA, the AMF/ANF/AG material can also preferably be made of poly(ethylene glycol) (PEG), also known as poly(ethylene oxide) (PEO) or polyoxyethylene (POE). Caprolactone (CPL) can also be used. CPL and PEG are elastomeric materials and if the AMF/ANF/AG medical device has elastomeric properties it will better conform to the natural shape of the lumen in which it is inserted or implanted. Elastomeric materials are better able to close gaps between an implant wall and a lumen wall. Avoiding incomplete apposition of the implant implants against the lumen wall reduces the formation of stagnant pockets in which a thrombus is more likely to develop. Metallic implant implants are typically stiff and cannot conform well to the lumen when the lumen is not smooth and uniform, as is often the case. However, an elastomeric coating upon non-elastomeric implant implants ameliorates this problem by flexing, bending, expanding, and contracting to occupy the differential spaces created by the nonconformity between the lumen wall and the implant implants. Alternatively, if the implant implants themselves are made of AMF/ANF/AG elastomeric materials they can directly model the irregular surface patterns of anatomic lumens.

The AMF/ANF/AG material can also be made out of biological molecules (biomolecules) such as collagen, fibrin, or fibrinogen. Various other substances that can be used to form the AMF/ANF/AG material are: phosphorylcholine, nitric oxide, high density lipoprotein, polyzene-F, PTFE polyetherester, hydroxyapatite, polyhydroxy-butyrate, polycaprolactone, polyanhydride, poly-ortho ester, polyiminocarbonates, polyamino acids, and polyvinyl alcohol.

Irrespective of the chemical components used to form the AMF/ANF/AG material, when used as a delay coating the AMF/ANF/AG material is preferably negatively charged and also preferably has a nitric oxide functional group. Thus, as the fibers degrade, nitric oxide is released. Within the bloodstream of the lumen occupied by the implant, the nitric oxide serves to further inhibit restenosis by preventing platelet aggregation and macrophage/leukocyte infiltration, reducing smooth muscle cell proliferation, and decreasing inflammation generally while aiding the healing process. An aligned coating with a nitric oxide group (ANO) on an implant (or other intravascular medical device) forms an artificial endothelium layer due to the smooth, streamlined surface the aligned fibers/grooves provide coupled with the ability of nitric oxide to prevent aberrations on this smooth surface as the fibers degrade.

The inventor recognizes the use of any biocompatible materials that can be formed into aligned nanofibers, aligned microfibers, or aligned grooves for the AMF/ANF/AG material used to form an implant, a coating, or a matrix for therapeutic agent(s). The present invention also recognizes the ability to use the AMF/ANF/AG material in conjunction with other coatings, layers, matrices, pores, channels, reservoirs, etc. to delay onset of the release of any therapeutic agent and/or to encourage structured (i.e. aligned) endothelization.

The present invention also teaches the criticality of matching the time period of delay prior to therapeutic agent release with the time it takes for the AMF/ANF/AG implant surface to become covered (i.e. encapsulated) by endothelization to a depth of approximately 0.1 mm. The artificial functional endothelium layer itself is a very thin (i.e. only one or a few cells thick). A thin layer does not burden the implant with unnecessary volume (i.e. on the periphery of a cross-section) that could make insertion and adjustment within the lumen more difficult. A thin layer also does not significantly reduce the inner diameter of the implant's lumen and therefore does not interfere with hemodynamics or obstruct blood supply to a treated area.

When the implant is not formed of a material (i.e. such as an elastomeric aligned material) that enables it to conform to the shape of a lumen surface, a thrombus is more likely to develop causing a localized inflammatory reaction. Also, when the implant doesn't conform well to the shape of a lumen, the process of restenosis cannot be effectively controlled. Although systematic therapeutic agents administered with BMS and therapeutic agents supplied by DES can slow or modulate the rate of ineffective restenosis they are not typically used to encourage a moderate amount of beneficial restenosis. Any restenosis that does occur in a vessel having an uneven surface with implant implants that inadequately conform to the natural cell and protein structure (and/or shape) of the vessel is likely to be uncontrollable and problematic. Smooth muscle cell migration and proliferation is likely to form the first tissue layer over the implant implants. In contrast, the present invention provides a preformed artificial functional endothelial layer to provoke a first in vivo layer of natural endothelial cell growth.

In some embodiments, a drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—CO2R, where P is the polymer backbone and R is an alkyl group having from 1 to 4 carbons.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

In some embodiments, the teachings are directed to a medical device having a drug-retaining coating that at least substantially delays the initial elution of a drug for a time effective at forming a functional endothelium over a surface of the medical device. In some embodiments, the coatings are a switch for "turning on" drug elution at a desired time, where the switch can be programmed through coating design to elute at the desired time using the methods taught herein. In some embodiments, the coating can be designed to elute at a desired rate after the onset of elution.

In some embodiments, a coating "at least substantially delays the initial elution" includes, for example, where there is no measurable elution of drug for an initial period of time, or the elution of drug over the initial period of time is negligible or sufficiently retained, such that the desired effect that would be obtained in the absence of any drug elution is still obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. And, "a time effective at forming a functional endothelium over a surface of the medical device" can be, for example, any duration of time in which the elution of drug can be entirely or partially inhibited to allow for formation of an endothelium that provides a localized source of thrombomodulin where desired, in an area of an implant. In some embodiments, the terms "block", "delay", and "retain" can be used interchangeably.

The coating can comprise a drug-containing layer applied over a surface of the medical device. In some embodiments, the drug-containing layer can be 100% drug. In some embodiments, the drug-containing layer can comprise 5, 10, 15, 20, 25, 30, 35, 40, 45, 50, 55, 60, 65, 70, 75, 80, 85, 90, 95, 99, 100 percent drug, or any amount therein.

The surface of the medical device can include any surface of a medical device, such as an implanted medical device. The surface may be, for example, a breast or buttock implant, in some embodiments. The drug-containing layer can be used to provide a drug that functions as an anti-proliferative agent; and, a drug-reservoir layer can be applied over the drug-containing coating.

In some embodiments, the HA-PVA hydrogel can comprise a drug-retaining layer that is void or substantially void of the drug at a time of implantation in a subject. A layer can be considered "substantially void" of the drug where the layer has an almost immeasurable amount of drug in the layer, or the amount is so small that the effect on the delay in onset of drug elution is still controllable using the coatings and methods taught herein. In some embodiments, a layer is substantially void of the drug, where the amount of drug is negligible or sufficiently small, such that the desired effect of the delay in the onset of elution would be obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. In some embodiments, a layer is substantially void of drug where the drug composes less than 2.0, 1.0, 0.8, 0.6, 0.5, 0.4, 0.3, 0.2, 0.1, 0.09, 0.08, 0.07, 0.05, 0.03, 0.01, 0.001 percent of the layer, or any amount therein.

The teachings are naturally directed to include a therapeutic coating that promotes formation of a functional endothelium on a medical device. The coating comprises a biodegradable drug-containing layer that is positioned over a surface of a medical device and serves as a source of a drug that functions as an anti-proliferative agent in a subject. The coating can also comprise a biodegradable drug-reservoir layer positioned over a surface of the drug-containing layer. The drug-reservoir layer can comprise a drug-retaining layer, wherein the drug-retaining layer can be void or substantially void of the drug at a time of implantation in the subject and function to retain and at least substantially block an initial release of the drug into the subject for a time sufficient to form a functional endothelium over the surface of the medical device. As discussed, the functional endothelium can provide a beneficial source of thrombomodulin to the subject to an area affected by a medical device.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from implanted medical devices. Such parameters can vary the desired amount of time based on, for example, type of implant, location of implant, construction of implant, selection of drug, desired effect, and the like.

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly (hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly (N-vinyl pyrrolidone); poly(aminocarbonates); poly(iminocarbonates); poly(anhydride-co-imides), poly(hydroxyvalerate); poly(L-lactic acid); poly(L-lactide); poly (caprolactones); poly(lactide-co-glycolide); poly (hydroxybutyrates); poly(hydroxybutyrate-co-valerate); poly(dioxanones); poly(orthoesters); poly(anhydrides); poly (glycolic acid); poly(glycolide); poly(D,L-lactic acid); poly (D,L-lactide); poly(glycolic acid-co-trimethylene carbonate); poly(phosphoesters); poly(phosphoester urethane); poly(trimethylene carbonate); poly(iminocarbonate); poly (ethylene); poly(propylene) co-poly(ether-esters) such as, for example, poly(dioxanone) and poly(ethylene oxide)/poly (lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly (ethylene-co-vinyl alcohol) (EVAL), copolymers of acrylonitrile-styrene, ABS resins, and copolymers of ethylene-vinyl acetate; poly(amides) such as Nylon 66 and poly (caprolactam); alkyd resins; poly(carbonates); poly (oxymethylenes); poly(imides); poly(ester amides); poly (ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly(D,L-lactide-co-PEG) block copolymers, poly(D, L-lactide-co-trimethylene carbonate), polyglycolides, poly (lactide-co-glycolide), polydioxanones, polyorthoesters, polyanhydrides, poly(glycolic acid-co-trimethylene carbonate), polyphosphoesters, polyphosphoester urethanes, poly (amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—CO2R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, isooctyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containining groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following implantation of a metal or polymer drug-eluting medical device. In some embodiments, the medical device comprises an implant.

It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope the invention.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin IL actinomycin X1, actinomycin C1, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MUTAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists, fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono-di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight. The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents. It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

While certain embodiments use gamma irradiation or electron beam (e-beam) sterilization, other types of radiosterilization can be used.

The above described HA-PVA hydrogel provides a natural feel through viscoelastic harmony of properties between the existing tissue and the implant. This can be done by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hyper-volumic degradation, anatomic compliant and iso-osmotic controlled, among others.

The present invention has been described particularly in connection with a breast, butt, or body implant, among others, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

The methods are applicable to the creation of materials for use in medical, biological and industrial areas including the controlled delivery of agents (which may include proteins, peptides, polysaccharides, genes, DNA, antisense to DNA, ribozymes, hormones, growth factors, a wide range of drugs, imaging agents for CAT, SPECT, x-ray, fluoroscopy, PET, MRI and ultrasound), generation of load bearing implants for hip, spine, knee, elbow, shoulder, wrist, hand, ankle, foot and jaw, generation of a variety of other medical implants and devices (which may include active bandages, transepithelial drug delivery devices, sponges, anti-adhesion materials, artificial vitreous humor, contact lens, breast implants, stents and artificial cartilage that is not load bearing (i.e., ear and nose)), any application where gradients (single or multiple) in mechanical properties or structure are required.

Variations and modifications can, of course, be made without departing from the spirit and scope of the invention. For example, the HA-PVA gel can be used as facial fillers, dermal fillers, butt fillers, breast fillers, and other body part fillers. The implants of the present invention further can be instilled, before or after implantation, with indicated medicines and other chemical or diagnostic agents. Examples of such agents include, but are not limited to, antibiotics, chemotherapies, other cancer therapies, brachy-therapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast, butt, or body implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement. The other methods, used for characterization of the products according to one embodiment are described in the following examples which illustrate preferred embodiments of one embodiment without, however, being a limitation thereof.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. A method for body augmentation, comprising:
storing a non-toxic biocompatible material;
storing a biocompatible polymer having a multi-phase mixture with a predetermined controlled release of selected pharmaceutical substance to modulate soft tissue response to the polymer;
mixing the biocompatible material and polymer to crosslink the mixture by exposing HA-PVA (hyaluronic acid-polyvinyl alcohol) hydrogel to an amount of ionizing radiation providing a radiation dose effective to crosslink the HA to the PVA and providing a mask; and
augmenting soft tissue with the cross-linked mixture.

2. The method of claim 1, wherein the polymer comprises one of: hyaluronic acid, polyvinyl alcohol, collagens, PEG, hyaluronic acids, celluloses, proteins, saccharides, biodegradable and bioresorbable biocompatible materials.

3. The method of claim 1, comprising mixing an anti-inflammatory compound or an antiproliferative compound.

4. The method of claim 1, comprising injecting the cross-linked mixture directly into breast tissue or into a breast implant to augment the soft tissue.

5. A method of making a cross-linked hydrogel comprising:

storing a biocompatible material and storing a biocompatible polymer having a multi-phase mixture with a predetermined controlled release of selected pharmaceutical substance to modulate soft tissue response to the polymer;

mixing hyaluronic acid (HA) with polyvinyl alcohol (PVA) to form an HA-PVA (hyaluronic acid-polyvinyl alcohol) hydrogel; and exposing the HA-PVA hydrogel to an amount of energy effective to crosslink the HA and the PVA and to sterilize the container content.

6. The method of claim 1, wherein the exposing comprises performing one or more freeze-thaw cycles to HA-PVA (hyaluronic acid-polyvinyl alcohol) hydrogel.

7. The method of claim 1, comprising performing one or more freeze-thaw cycles to HA-PVA (hyaluronic acid-polyvinyl alcohol) hydrogel and then autoclaving the HA-PVA hydrogel.

8. The method of claim 1, comprising first autoclaving the HA-PV hydrogel and then performing one or more freeze-thaw cycles to HA-PVA hydrogel.

9. The method of claim 1, comprising exposing the HA-PVA hydrogel to sterilize the container content.

10. The method of claim 9, comprising exposing the irradiated HA-PVA hydrogel to a temperature above the melting point of a PVA crystalline phase to produce a cross-linked hydrogel.

11. The method of claim 9, wherein the ionizing radiation is X-ray, e-beam, gamma radiation or beta particles.

12. The method of claim 1, comprising providing an irradiation mask, a step mask, or a gradient mask.

13. The method of claim 9, comprising performing at least one freeze-thaw cycle to the HA-PVA hydrogel.

14. The method of claim 1, comprising mixing a slow release anti-inflammatory agent to the HA-PVA hydrogel.

15. The method of claim 1, comprising:
dissolving the HA-PVA hydrogel in a solvent;
heating the HA-PVA hydrogel to a temperature elevated above the melting point of the PVA and inducing gelation of vinyl polymer at a rate to form crystalline physical associations in the HA-PVA hydrogel;
exposing the physically associated vinyl polymer hydrogel to a dose of radiation effective to produce covalent crosslinks; and
autoclaving the HA-PVA hydrogel to remove physical associations and forming a covalently cross-linked HA-PVA hydrogel.

16. A method, comprising
storing a non-toxic biocompatible material and a biocompatible polymer having a multi-phase mixture with a predetermined controlled release of selected pharmaceutical substance to modulate soft tissue response to the polymer;
mixing the biocompatible material and polymer to cross-link the mixture;
forming a biocompatible cross-linked polymer having an interpenetrating polymer network (IPN) including:
cross-linking a heteropolysaccharide to form a single cross-linked material; and
performing one or more additional cross-linkings on the single cross-linked material to form a multiple cross-linked material,
wherein the multiple cross-linked material has one or more IPN regions resisting biodegradation in a human body than the single cross-linked material and one or more single cross-linked extensions radiating out from the IPN, wherein the combination of the IPN and the extension provide one or more of: biodegradation resistance, soft touch feeling, ease of insertion into the human body and augmenting soft tissue with the cross-linked mixture.

17. The method of claim 1, comprising dispensing ciproflaxin uniformly throughout the HA-PVA hydrogel.

18. The method of claim 1, wherein the mixing comprises adding one or more of: an anesthetics, a lidocaine, a compound to reduce or eliminate acute inflammatory reactions, and a composition selected from the group consisting of steroids, corticosteroids, dexamethasone, triamcinolone.

19. The method of claim 16, comprising:
mixing hyaluronic acid (HA) with polyvinyl alcohol (PVA) to form an HA-PVA hydrogel; and
exposing the HA-PVA hydrogel to one or more freeze-thaw cycles or to an amount of radiation effective to crosslink the HA to the PVA.

20. The method of claim 19, wherein the radiation comprises X-ray, e-beam, gamma radiation or beta particles.

* * * * *